(12) United States Patent
Treco et al.

(10) Patent No.: US 6,242,218 B1
(45) Date of Patent: Jun. 5, 2001

(54) GENOMIC SEQUENCES FOR PROTEIN PRODUCTION AND DELIVERY

(75) Inventors: Douglas A. Treco, Arlington; Michael W. Heartlein, Boxborough; Richard F Selden, Wellesley, all of MA (US)

(73) Assignee: Transkaryotic Therapies Inc., Cambridge, MA (US)

( * ) Notice: Subject to any disclaimer, the term of this patent is extended or adjusted under 35 U.S.C. 154(b) by 0 days.

(21) Appl. No.: 09/305,384

(22) Filed: May 5, 1999

Related U.S. Application Data

(60) Provisional application No. 60/084,649, filed on May 7, 1998.

(51) Int. Cl.$^7$ ..................................................... C12P 21/02
(52) U.S. Cl. ........................ 435/69.4; 435/69.6; 435/463; 435/325; 435/320.1
(58) Field of Search .............................. 435/320.1, 325, 435/463, 69.4, 69.6; 514/44

(56) References Cited

U.S. PATENT DOCUMENTS

| 5,641,670 | 6/1997 | Treco et al. | 435/325 |
| 5,733,761 | 3/1998 | Treco et al. | 435/440 |

FOREIGN PATENT DOCUMENTS

WO 95/31560  11/1995  (WO).

OTHER PUBLICATIONS

Orkin et al., "Report and Recommendations of the Panel to Assess the NIH Investment in Research on Gene Therapy", Dec. 1995, National Institutes of Health.*
Editorial, *Nature Biotechnology*, vol. 15, Sep. 1997, p. 815.*
Verma et al., *Nature*, vol. 389, Sep. 1997, pp. 239–242.*
Kershaw et al., "Human DNA Sequence from Cosmid U221F2 on Chromosome X. Contains ESTs and STS," EMBL Database Entry HSU221F2, Accession No. Z75746, XP002110689, Abstract (1996).
Arakawa, Tsutomu et al., "Structure and Activity of Granulocyte Colony–Stimulating . . . ," Archives of Biochemistry and Biophysics, vol. 316, No. 1, pp. 285–289, Jan. 10, 1995.
Kulmberg, Peter et al., "Cloning and sequence analysis of the immediate promoter . . . ," Gene, vol. 197, p. 361–365, (1997).
Kuczek, Elizabeth S. et al., "A Granulocyte–Colony–Stimulating Factor Gene Promoter . . . ," The Journal of Immunology, vol. 146, No. 7, p. 2426–2433, Apr. 1, 1991.

Leizer, Tali et al., "Cytokine Regulation of Colony–Stimulating Factor Production . . . ," Blood, vol. 76, No. 10, pp. 1989–1996, Nov. 15, 1990.
Monaco, Lucia et al., "Expression of recombinant human granulocyte colony–stimulating factor . . . ," Gene, vol. 180, p. 145–150, (1996).
Nishizawa, Mikio et al., "Regulatory Elements Responsible to Inducible Expression of the . . . ," Molecular and Cellular Biology, vol. 10, No. 5, p. 2002–2011, May 1990.
Nagata, Granulocyte Colony–Stimulating Factor, In: Peptide Growth Factors and Their Receptors, Sporn and Roberts (eds.), Springer–Verlag, New York, NY, pp. 699–722, 1991.
Nagata, Shigekazu et al., "Molecular cloning and expression of cDNA for human . . . ," Nature, vol. 319, p. 415–418, Jan. 30, 1986.
Nagata, Shigekazu et al., "The chromosomal gene structure and two mRNAs for . . . ," The EMBO Journal, vol. 5, No. 3, pp. 575–581, 1986.
Reidhaar–Olson, John F. et al., "Identification of Residues Critical to the Activity of . . . ," Biochemistry, vol. 35, No. 28, p. 9034–9041, 1996.
Rotondaro, Luigi et al., "High–level Expression of a cDNA for Human Granulocyte . . . ," Molecular Biotechnology, vol. 7, p. 231–240, 1997.
Stanley, Edouard et al., "The structure and expression of the murine gene encoding . . . ," The EMBO Journal, vol. 4, No. 10, pp. 2569–2573, 1985.
Tweardy, David J. et al., "Molecular Cloning and Characterization of a cDNA for Human . . . ," Oncogene Research, vol. 1, pp. 209–220, 1987.
Tweardy, David J. et al., "Molecular Cloning of cDNAs for the Human Granulocyte . . . ," Blood, vol. 79, No. 5, pp. 1148–1154, Mar. 1, 1992.
Won Han, Sang et al., "Cloning and expression of the cDNA Encoding rat granulocyte . . . ," Gene, vol. 175, p. 101–104, 1996.

* cited by examiner

*Primary Examiner*—James Ketter
(74) *Attorney, Agent, or Firm*—Clark & Elbing LLP

(57) ABSTRACT

An isolated nucleic acid molecule that hybridizes under stringent conditions, or shares at least 80% sequence identity, with a defined genomic region upstream of the coding region of the G-CSF gene, and a DNA construct containing that DNA molecule as a targeting sequence for homologous recombination.

30 Claims, 10 Drawing Sheets

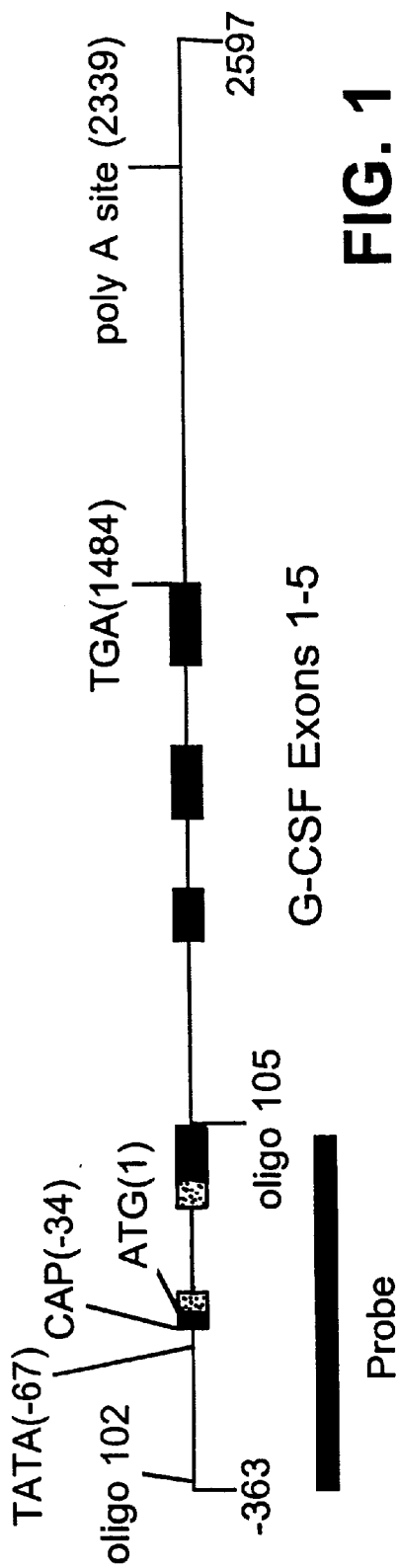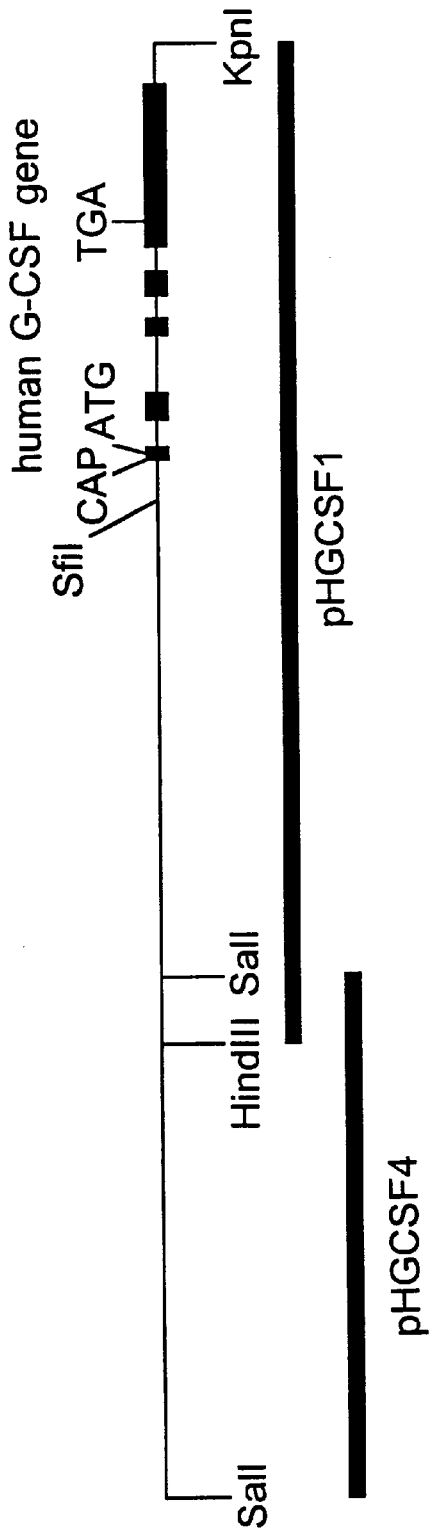

```
        SalI (-6596)
-6597   GTCGACCTGC AGTCAACGG ATCACTTGAG GACAGTAGTT CAAGACCAGC CTGGGCAGCA TAGGGAGACT GTCTCTACGA AAAATCAAAA AATTATGCC
-6497   GGGCATGGTG GCTCACGTCT GTAATCCCTG AACTTTGGGA AGTTGCCAGC ATGGTGGCAG CATCAAGGCA AGTGGATCAC TTGAGGTCAG GAGTTCGAGA CTAGCCTGGC CAACATGTG
-6397   AAACCCTATC TCCACTAAAA AATACAAAAA TTAGCCAGGC GATCACACCA CTGCACTCCA GCCTGGGTGA TCCCGGCTAC CAGAGCAAGA AAAAAATAA AATCACTTGA
-6297   ACCCAGAGG CGGAGGTTGC AGTGAGCTGA TGCACACCTC TAGTCTCAGC CTCACTCAGG AGCTCAGGAG GCTGAGGTGG CAGAGCAAGG CTACAGTGAG
-6197   AAATTAGCCA GGCATGGTAG GCCACTACAC TCCAGCCTGG GCAACAGAGA GCAAACTC AAAGATCCAG ATAATAATAA AACAGCTCTG TTTATGTCTC
-6097   CCAAGATCAT GCCACTACTA CATACTACTA TGTATATAGT TTGCAAACTC AAAGATCCAG ATAATAATAA TTTTAGGCTT GTGTCTCTGT CACAATCACT
-5997   CTGGTCCATA CATACTACTA AAAAGCAGCT ATAAACAATA CATACATGAA TTTTTATAG ACATCGAGAT GTGGGCCGTA TTGATTTTTT ACATTTTATA
-5897   CTGCCCTGTC TTTCTAGCAC AAAAGCAGCT ATAAACAATA TGTAAAAAGC GGCCAGCGCG CCATCGTCAC GCCTTGTAAT CCAGCACTTT GGGAGGCTGA
-5797   AAATAATCTT TTTAAAAATT TTCCCCTAAC CATTTAAAAG TGTAAAAAGC GGCCAGCGCG CCATCGTCAC GCCTTGTAAT AAAAATAAAA GGCATAGTGG
-5697   GGTGGGCAGA TCACTTGAGA TCAACAGTTC GAGACCAGCC TGGCCAACAT AGCAAAACCC CATTTCTACT CATTCTACT AATTAGCTG CCACTGCACT
-5597   TGCACACCTG TGATCCCAGC TACTTGGGAG GCTGAGGCAG TCAACGAGCT TGAACCTGGG GAGAGCTCGCT AAGCGGAGGT TGCAGTGAGC CAACATCATG CAGGTCTGCG
-5497   CCAGCCTGGG TGACAGAGTG AGACTTCGTC TCAAACAAAA AAAAAAGTGT AAAAGCCATT CCTAATTCAG TGTACATACT CCAAGTTGCC ATCAAGGAG
-5397   TACTCCTGCT CTGAGGCATA CCTGAGAAGT TGCTTAGGTC AGAGTTACTC GCAACAAATG GGTCACAGGA CATACACTTC CAGATCCTTT ACAAAGATGC CTAAGCCCA GTACCAGATG AAAACAGAA
-5297   GTTTTTTT TACAATCTAC ACTCCCCCCA CCCCTTCTAA CCATGAAGAA ATACTGGTA TCTCAGCCCC ATGTGTCATG GCCAGTGATA GGATGAATAA CGGGGTCTC TGGAGCGCTC
-5197   GTGGAGGGG AAGCTGCCAG ATCACTGTGA CTTCTGAGCC GCAACAAATG TCCAGATCCAG CAAGATGTAC AGGGAAAAGT ACAGGAGATA CTTCTCTGAG ACTCTCTGTT TGTCTTTAT
-5097   CCCCTGTCAG TCTCCCCATG TGGGGCTGAA GTCTGGATTG AGCCGTTATT TCCAGATCCAG CAAGATGTAC AGCTTTCTTG ACAGGAAAAGT AAACAGCAGG GGCTTGGCAA
-4997   TCTCCCCATG CTGCAAATCC CTGCAAATCC TACCTGGCTC AGCCACCAGC TAGTTCTGTG ATCTTGAACA AGTTTTTCA CTTCTCTGAG GCCATCCTTT GGCTACAACA
-4897   GATGATCTAA CTGCAAATCC TTGACAGGAT GAAATGACGA AGTCCCTTAC CCAGCACTTT ACAAAGATGC CTAAGCCA GGATGAATAA CGGGGTCTC TGGAGCGCTC
-4797   CACCAGTTGG TTGACAGGAT GAAATGACGA AGTCCCTTAC CCAGCACTTT ACAAAGATGC GATGCTGGAA GCCAGTGATA CGGGGTCTC TGGAGCGCTC GGCTACAACA CTGAGAGGTG
        SphI (-4693)
-4697   ACAGCATGCC GGCAGTCCTC TTCGCTCTCG GCGCCTCCTC TGCCTGGGCT CCCACTTCGG TGGCACTTGA AGCCCACCGC
-4597   TGCACTGTGG GAGCCTGGC CAAGGCCAGA CTGGGCTGCC GCCGGCTCCC TCAGCTTGCA GGGGAGGTGTG GAGGCAGAGG CTCAAGCAGG AACCGGGCT
                                                                                                        SmaI (-4406)
-4497   GCGCACGGGG CTTGCGGGCC AGCTGGAGTT CCGGGTGGGC GTGGGCTTGG CGGGCCCCCGC ACTCGGAGCA CCTGCCAGGC GCGGGGCCAGC CCCGGGCAAT
```

FIG. 3A

```
        Smal (-4383)
-4397 GAGAGGCTTA GCACCCGGGC CAGCGGCTGC GGAGGGTGTA CTGGGTTGCC CAGCAGTGCC AGCCCGCCGG CGCTGTGTCT GCTCGATTTC TCACTGGGCC
-4297 TTAGCAGCCT TCCCGCGGGG CAGGGCTCGG GACCTGCAGC CCGGCCATGCC TGAGCCTCCC CTCATGGGC TCCTGTGCGG CCCGAGCCTC CCCGACGAGC
-4197 ACCACCCCCT GCTCCACAGC GCCCAGTTCC ATCGACCACG CAAGGGCAC GAAGTGCGGG CGCACTGGC AGGCAGCTAC CCCTGCAGCC
-4097 CTGGTGCGGA ATCCACTGGG TGAAGCCAGC TGGGCTCCTG AGTCTGGTG AGACTTGGAG TCTAGCTCAG GGATCGTAAA TACACCAATC
-3997 AGCACCCTGT GTCTAGCTCA GGGTCTGTGA ATGCACCAAT CCCACACTCG TATCTAGCTA CTCTGATGGG GCCTAGCTCA ACCTTTATGT CTAGCTCAG
-3897 GATTGTAAAT ACACCAATCG GCACTCTGTA TCTAGCTCAA GGTTTGTAAA CACACCAATC AGCACCCTGT GTCTAGCTCA GGGTATGTGA ATGCACCAAT -3797 CGACAGTCTG TATTCGGCTA CTTTCATGGG CATCCGTGTG AAGAGACCAC CAAACAGGCT AATAAAGCTT CTATCACCTG GGTGCAGGTG
-3697 GGCTGAGTCC GAAAAGAGAG TCAGCGAAGG AGATAAGGGT TATAGATTT GGGGCCGTTT TATGTGAGC CAGTCAAAGG GGGTTGTTC
-3597 TCTGGCCGGG CAGGAGTGGG GCCCAGTCCC GTGCTCAGTG GGGGTGCTTT TTGAGCCAGG ATGAGCCAGGC AAAAGGACTT TCACAAGGTA ATGTCATCAA
-3497 TTAAGGCAAG GACCCGCCAT TTGTGGTGG AATGTCATCA GTTAAGTTC GGGGCAGGGC ATATTCACTT CTTTGTGAT TCTTTCGTTA
-3397 CTTCAGGCCA TCTGGGCGTA TTACAGGGGA TGCCATGGCT TGGCTTGGGC TCAGAGGCTT GACAGCTACT CTGGTGGGC CTTGGAGAAT
                                                        HindIII (-3722)

-3297 GTTTGTGTCG ACACTCTGTA TCTAGTTAAT CTAGTGGGGA CGTGGAGAAC CTTTGTGTCT AGCTCAGGGA TTGTAAACGC ACCAATCAGC GCCCTGTCAA
-3197 AACAGACCAC TCGGCTCTAC CAATCAGCAG GATGTGGGTG GGGCCAGATA AGAGAATAAA AGCAGGCTGC CCGAGCCAAC AGTGGCAACC GCACAGTCC
-3097 CTATCCACAA TATGGCAGCT TTGTTCTTTT GCTCGTTGCG ATAAATCTTG CTACTGCTCG CTTTTTGGGT CCACACTGCT TTTATGAGCT GTAACACTCA
-2997 CCACGAAGGT CTGCAGCTTC ACTCCTGAAG CCACTAAGAC CCGAGAGAAT GAACAACTCC GGCCGGCTG CCTTAAGAGC ACATCAGAAG TATAACACTC
-2897 ACCGCGAAGG TCTGCAGCTT CACTCCTCAG CCAGCGAGAC CACGAAGGAA GAAACTGCAA AGTCAGTGAG ACATCAGAAG ACACATCTGA GAACAAACTC
-2797 CAGATGCACC ACCTTAAGAG CTGCAGCGCT TCCTTCTTGA GTCAGTGAG ACCAAGCACT ACCAAGCACT AGTCAGTGAG GGACACAAGC
-2697 CCAGGAGTTT GAGATCAGCC TGGCAACAT CCTCTCTCA AAAAAAAAA AATTACAAA AATTACAAA GTCGGTGTC CGTGGCCTGT
-2597 GGTCCCAGCT AGCGGAGCC AGGATCGCTT TGGGCAACAT GAGCTGAGCT GGTGAAGACT GCAGTGAGCT GTGATTGTAC CACAGCCCTC TAGGCTGGGG
-2497 GACAGACTGA GACCCTGTTT CCCCTCCGCA AAAAAATTGA CAAAAGTGTA ATAAGAGGTG CCTGATATGG CTAGGTGCAG CTGCTCATGC CTGTAATCCC
-2397 AGCACTTTGG GAAGCCGAGG ACCTAAGGTC AGGAGTGTGA GACCAGCCTG GCCAACATGG AGAAAGCCCA TCTCTCTAA AAATACAAAA
                Sphl (-2269)

-2297 TTAGCCGGCT GTGGGGCAG TGCCTGTAAT CCCAGCTACT CAGGAGGCTG AGGCAGGAGA ATCACTTGAA CCCAGGAGGC GGCGGTTGCA
-2197 GTGAGCCGAG ATCGTGCCAT TGCACTCCAC TGGGCCAACA CTGTGTTAA AAGCCCAAC AAAAAAAA AAGTGCCTG ACATATAAGA
-2097 GGTGTGCAAT GCATAGTTGC GCATAGTTGC GTTTAAGAAT GTGGAGCTCC TGCCTTCCAT GGTCCTGTA AAACCCACC CTCAAGGCCA GGTGCAGTGG
-1997 CTCATGCCTA TAATCCCAGC ACTTTGGGAG GCCGAGGCGG GTGGATCACC GTGGAGTCAGG AGTTCGAGAC CAGCCTGACC ACCAACATGG TGAAATCCCA
```

```
GATCACTTGAGGACAGTAGTTCAAGACCAGCCTGGGCAGCATAGGGAGACTGTCTCTACGAAAAA
TCAAAAAATTATGGCCGGGCATGGTGGCTCACGTCTGTAATCCCTGAACTTTGGGACATCAAGGC
AAGTGGATCACTTGAGGTCAGGAGTTCGAGACTAGCCTGGCCAACATGGTGAAACCCTATCTCCA
CTAAAAAATACAAAAATTAGCCAGGCATGGTGGCAGGCACCTGTAATCCCGGCTACTCAGGAGGC
TGAGGCAGGAGAATCACTTGAACCCAGGAGGCGGAGGTTGCAGTGAGCTGAGATCACACCACTGC
ACTCCAGCCTGGGTGACAGAGCAAGACTCTATCTCAAAAAAAATAAAAAAATAAAAAAATTAGCC
AGGCATGGTAGTGCACACCTCTAGTCTCAGCTACTCAGGAGGCTGAGGTGGGAGGATCACTTGAA
CCTGGGGCAGTCAAGGCTACAGTGAGCCAAGATCATGCCACTACACTCCAGCCTGGGCAACAGAG
AGAGACCCTGTCTCTAAAAAAATAATAATAATAAAGAAAAAAACAGCTCTGTTTATGTCTCCTGG
TCCATACATACTACTATGTATATAGTTTGCAAACTCAAAGATCCAGATAGTCAATTTTTTAGGCT
TGTGGGCCGTATGGTCTCTGTCACAATCACTCTGCCCTGTCTTTCTAGCACAAAAGCAGCTATAA
ACAATACATACATGAATTTTTATAGACATCGAGATTTGAATTTCATATGATTTTTACATTTTAT
AAAATAATCTTTTAAAAATTTTCCCCTAACCATTTAAAAGTGTAAAAGCCGGCCAGGGCGCCAT
CGTCACGCCTGTAATTCCAGCACTTTGGGAGGCTGAGGTGGGCAGATCACTTGAGATCAACAGTT
CGAGACCAGCCTGGCCAACATAGCAAAACCCCATTTCTACTAAAAATAAAAAAATTAGCTGGGCA
TAGTGGTGCACACCTGTGATCCCAGCTACTTGGGAGGCTGAGGCAGGAGAATCGCTTGAACCTGG
GAAGCGGAGGTTGCAGTGAGCCAACATCATGCCACTGCACTCCAGCCTGGGTGACAGAGTGAGAC
TTCGTCTCAACGAAAAAAAAAAGTGTAAAAGCCATTCCTAATTCAGTGTACATCAGTGTACATAC
TCAGGTCTGCGTACTCCTGCTCTGAGGCATACCTGAGAAGTAGAGTTGCTTGGTCACAGGACATA
CACATTTCCACATTAACTAGACACTACCAAGTTGCCATCCAAGGAGGTTTTTTTTTACAATCTA
CACTCCCCCCAGCAACAAATGAGAGTTACTCCAGATCCTTTACAAAGATGCTCTAAGCCCAGTAC
CAGATGAAAACAGGAAGTGGCAGGGAAGCTGCCAGCCCCTTCTAACCATGAAGAAATACCTGGT
AGAGCCTTCTGGATGCTGGAAGGATGAATAACGGGGGTCTCTGGAGCCTGCCCCCTGTCAGATCA
CTGTGACTTCTGAGCCTCCAGTCCAGTCTCAGCCCCATGTGTCATGGCCAGTGATAATGAGCCCT
CACTCTCTGTTTGGTCTTTATTCTCCCCATGTGGGCTGAAGTCTGGATTGAGCCGTTATTCAAG
ATGTACAGCTTTCTTGACAGGAAAGTAGTGTCACAGAAACAGCAGGGGCTTGGCAAGATGATCTA
ACTGCAAATCCTACCTGGCTCAGCCACCAGCTAGTTCTGTGATCTTGAACAAGTTTTTTCACTTC
TCTGAGGCCATCCCTTGGCTACAACACACCAGTTGGTTGACAGGATGAAATGACGAAGTCCCTTA
CACCTGTAATCCCAGCACTTTGGGAGGCCAAGGCGGGTGGATGGCTTGAGCCTGAGAGGTGACAG
CATGCCGGCAGTCCTCACAGCCCTCGTTCGCTCTCGGCGCCTCCTCTGCCTGGGCTCCCACTTCG
GTGGCACTTGAGGAGCCCTTCAGCCCACCGCTGCACTGTGGGAGCCCCTTTCTGGGCTGGCCAAG
GCCAGAGCCGGCTCCCTCAGCTTGCAGGGAGGTGTGGAGGGAGAGGCTCAAGCAGGAACCGGGGC
TGCGCACGGCGCTTGCGGGCCAGCTGGAGTTCCGGGTGGGCGTGGGCTTGGCGGGCCCCGCACTC
GGAGCAGCGGGCCAGCCCTGCCAGGCCCCGGGCAATGAGAGGCTTAGCACCCGGGCCAGCGGCTG
CGGAGGGTGTACTGGGTGCCCCAGCAGTGCCAGCCCGCCGGCGCTGTGCTCGCTCGATTTCTCAC
TGGGCCTTAGCAGCCTTCCCGCGGGGCAGGGCTCGGGACCTGCAGCCCGCCATGCCTGAGCCTCC
CCTCCATGGGCTCCTGTGCGGCCCGAGCCTCCCCGACGAGCACCACCCCCTGCTCCACAGCGCCC
AGTCCCATCGACCACGCAAGGGCTGAGAAGTGCGGGCGCACGGCACCGGGACTGGCAGGCAGCTA
CCCCTGCAGCCCTGGTGCGGAATCCACTGGGTGAAGCCAGCTGGGCTCCTGAGTCTGGTGGAGAC
TTGGAGAACCTTTATGTCTAGCTCAGGGATCGTAAATACACCAATCAGCACCCTGTGTCTAGCTC
AGGGTCTGTGAATGCACCAATCCACACTCTGTATCTAGCTACTCTGATGGGCCTTGGAGAACCT
TTATGTCTAGCTCAGGGATTGTAAATACACCAATCGGCACTCTGTATCTAGCTCAAGGTTTGTAA
```

FIG. 5A

```
ACACACCAATCAGCACCCTGTGTCTAGCTCAGGGTATGTGAATGCACCAATCGACAGTCTGTATC
TGGCTACTTTCATGGGCATCCGTGTGAAGAGACCACCAAACAGGCTTTGTGTGAGCAATAAAGCT
TCTATCACCTGGGTGCAGGTGGGCTGAGTCCGAAAAGAGAGTCAGCGAAGGGAGATAAGGGTGGG
GCCGTTTTATAGGATTTGGGTAGGTAAAGGAAAATTACAGTCAAAGGGGGTTTGTTCTCTGGCGG
GCAGGAGTGGGGGTCGCAAGGTGCTCAGTGGGGGTGCTTTTTGAGCCAGGATGAGCCAGGAAAA
GGACTTTCACAAGGTAATGTCATCAATTAAGGCAAGGACCCGCCATTTACACCTCTTTTGTGGTG
GAATGTCATCAGTTAAGTTGGGGCAGGGCATATTCACTTCTTTTGTGATTCTTCAGTTACTTCAG
GCCATCTGGGCGTATATGTGCAAGTTACAGGGGATGCGATGGCTTGGCTTGGGCTCAGAGGCTTG
ACAGCTACTCTGGTGGGGCCTTGGAGAATGTTTGTGTCGACACTCTGTATCTAGTTAATCTAGTG
GGGACGTGGAGAACCTTTGTGTCTAGCTCAGGGATTGTAAACGCACCAATCAGCGCCCTGTCAAA
ACAGACCACTCGGCTCTACCAATCAGCAGGATGTGGGTGGGGCCAGATAAGAGAATAAAAGCAGG
CTGCCCGAGCCAGCAGTGGCAACGCGCACAGGTCCCTATCCACAATATGGCAGCTTTGTTCTTTT
GCTGTTTGCGATAAATCTTGCTACTGCTCGCTTTTTGGGTCCACACTGCTTTTATGAGCTGTAAC
ACTCACCACGAAGGTCTGCAGCTTCACTCCTGAAGCCACTAAGACCACGAGCCCACCGGGAGGAA
TGAACAACTCCGGCCGCGCTGCCTTAAGAGCTATAACACTCACCGCGAAGGTCTGCAGCTTCACT
CCTCAGCCAGCGAGACCACGAACCCACCAGAAGGAAGAAACTGCGAACACATCTGAACATCAGAA
GGAACAAACTCCAGATGCACCACCTTAAGAGCTGTAACACTCACTGCGAGGGTCCGCGGCTTCCT
TCTTGAAGTCAGTGAGACCAAGCACTCACCAGTTTCGGACACAAGCCCAGGAGTTTGAGATCAGC
CTGGGCAACATGATGAAATGCCCTCTCTGCAAAAAAAAAAAAAATTACAAAAATTGGCGGAGCAT
GGTGGTCCGTGCCTGTGGTCCCAGCTACGCGGGAGGCTAAAGTGGGAGGATCGCTTGAGCCTGGG
AGGTGAAGACTGCAGTGAGCTGTGATTGTACCACAGCCCTCTAGGCTGGGGGACAGACTGAGACC
CTGTTTCCCCTCCGCAAAAAAATTGACAAAAGTGTAATAAGAGGTGCCTGATATGGCTAGGCGCA
GTGGCTCATGCCTGTAATCCCAGCACTTTGGGAAGCCGAGGCGGGCGGGTCACCTAAGGTCAGGA
GTGTGAGACCAGCCTGGCCAACATGGAGAAAGCCCATCTCTTCTAAAAATACAAAATTAGCCGGC
TGTGGGGGCAGTGGTGGAGCATGCCTGTAATCCCAGCTACTCAGGAGGCTGAGGCAGGAGAATCA
CTTGAACCCAGGAGGCGGCGGTTGCAGTGAGCCGAGATCGTGCCATTGCACTCCACCCACTCCAG
CCTGGGCAACAAGAGCCAAACTCTGTCTTAAAAAAAAAAAAAAAAGTGCCTGACATATAAGAGG
TGTGCAATGCAATAGTTGCCAGGCAACATGTTTAAGAATGTGGAGCTCCTGCCTTCCATGGTCCT
GTTAAAAACCCACCCTCAAGGCCAGGTGCAGTGGCTCATGCCTATAATCCCAGCACTTTGGGAGG
CCGAGGCGGGTGGATCACCTGAGGTCAGGAGTTCGAGACCAGCCTGACCACCAACATGGTGAAAT
CCCACCTCTACTAAAAATACAAAATTAGATGAGCATGGTGGTGCATGCCTGTAATCCCACCTACT
TGGGAGGCTGAGGCAGGAAAATCACTAGAACCAGGGAGGCGGAGGTTGTAGTGAGCCGAGATCGT
GCCATTGCACTCCAGCCTGAGCAATGAGCGAAACTCCATCTCAAAAAAACAACAACAAAAACCCA
CTCTCTACTCCCAGGGAGCTGGGTACAGAGCTGGGCCACATCAGTGCAAGGTGCTGAGCCACAGA
GCTAAGGCGGAGCTGCAGGACCGCGGACCAGATAACAGTGTGTGAGATCAGTGTGTGAGATCAGA
CGTCCTGCCATTGGTGACCACCAGGGGGCCCCCAAGCACCAGAGATGGCCCCATCCAGTCACCA
CATCCACTTCTCATCCAGAGATGTCTGTTTCTTGGCACGCTGGGGTAAATTAGGACAGAAGGTGA
CAGTCTTGGGTGTGGTCAGTCAGACTGCCCCAGGCAGGCCTTGTGGCCTGTAGAAAACGTTCAGG
CCTAGGCCGGGCACGGTGGCTCACGCCTGTAATCCCAGCACTTTGGGAGGCCGAGGCGGGTGGAT
CACGAGGTCAGGAGATCGTGACCATCCTGGCTAACACGGTGAAACCCCGTCTCTACTAAAAATAC
AAAAAATTGGCCGGGCATGGTGGCGGGCACCTGTAGTTCCAGCTACTCGGGAGGCTGAGGCAGGA
GAATGGCGTGAACCCGAGAGGCAGAGTTTGCAGTGAGCCGAGATCGCGCCACTGCACTCCAGCCT
GGGCGACAGAGCAAGACTCCATCTGGAAAAGAAAAAGAAAACGTTCAGGTCTGAGCCAGAGGCCC
AGGCTGTAATTCTGTCACTTACCATGACCTTGGGCAAGGCACTTCCTTCCCTGGCCCAGTTCACG
GGGTTGGAATCGACTCCAAGGTCCCTTCCAGCATTAACGCTGCATGGTTCTAAGATGAGAAGATG
GGGCAGTTTCCCTCTCTCACCCCAGCCCGTGTCCACTTCAAGGTGAATGACCAGGGAAGTCACG
TGTCCCAATCCCGCAGTTCCAAAGCCCTTGGGGACCCTACTGTCAGGGTCGTGCACGAGGAGGTG
AAGGTCAGGTGAGCCAATCGCCTCGAAGGGTCTTGCCTCATTCGGGACAGACATCCGGTTTCCTC
TGGCTCTACCGGGATTCTAGGGGCTTTAGCCGAATGAGTCATGGGGGCGGGGGGTTTCTGGGG
GAGTTCCCAGCTAATCAACTTGGACAGGACAGCCTGGAACTTTCGATGGTGCCTATCCAAGTGT
GGGGTGGGCACAGCAGCCAAGACCCAATGTCCTTATCTCAGGTAGGGCTCAGGAGGTCTCCCAG
ACAGGCAGCCTCCGGAGAGTTTGGGGGTAGGAATGGGAGCAACCAGGCTTCTTTTTTCTCTCTT
AGAATTTGGGGCTTGGGGACAGGCTTGAGAATCCCAAAGGAGAGGGCAAAGGACACTCCCCC
ACAAGTCTGCCAGAGCGAGAGAGGGAGACCCCGACTCAGCTGCCACTTCCCCACAGGCCT
```

FIG. 5B

```
                                                              CC GGCAGTCCTC
ACAGCCCTCG  TTCGCTCTCG  GCGCCTCCTC  TGCCTGGGCT  CCCACTTCGG  TGGCACTTGA
GGAGCCCTTC  AGCCCACCGC  TGCACTGTGG  GAGCCCCTTT  CTGGGCTGGC  CAAGGCCAGA
GCCGGCTCCC  TCAGCTTGCA  GGGAGGTGTG  GAGGGAGAGG  CTCAAGCAGG  AACCGGGGCT
GCGCACGGCG  CTTGCGGGCC  AGCTGGAGTT  CCGGGTGGGC  GTGGGCTTGG  CGGGCCCCGC
ACTCGGAGCA  GCGGGCCAGC  CCTGCCAGGC  CCCGGGCAAT  GAGAGGCTTA  GCACCCGGGC
CAGCGGCTGC  GGAGGGTGTA  CTGGGTGCCC  CAGCAGTGCC  AGCCCGCCGG  CGCTGTGCTC
GCTCGATTTC  TCACTGGGCC  TTAGCAGCCT  TCCCGCGGGG  CAGGGCTCGG  GACCTGCAGC
CCGCCATGCC  TGAGCCTCCC  CTCCATGGGC  TCCTGTGCGG  CCCGAGCCTC  CCCGACGAGC
ACCACCCCCT  GCTCCACAGC  GCCCAGTCCC  ATCGACCACG  CAAGGGCTGA  GAAGTGCGGG
CGCACGGCAC  CGGGACTGGC  AGGCAGCTAC  CCTGCAGCC   CTGGTGCGGA  ATCCACTGGG
TGAAGCCAGC  TGGGCTCCTG  AGTCTGGTGG  AGACTTGGAG  AACCTTTATG  TCTAGCTCAG
GGATCGTAAA  TACACCAATC  AGCACCCTGT  GTCTAGCTCA  GGGTCTGTGA  ATGCACCAAT
CCACACTCTG  TATCTAGCTA  CTCTGATGGG  GCCTTGGAGA  ACCTTTATGT  CTAGCTCAGG
GATTGTAAAT  ACACCAATCG  GCACTCTGTA  TCTAGCTCAA  GGTTTGTAAA  CACACCAATC
AGCACCCTGT  GTCTAGCTCA  GGGTATGTGA  ATGCACCAAT  CGACAGTCTG  TATCTGGCTA
CTTTCATGGG  CATCCGTGTG  AAGAGACCAC  CAAACAGGCT  TTGTGTGAGC  AATAAAGCTT
CTATCACCTG  GGTGCAGGTG  GGCTGAGTCC  GAAAAGAGAG  TCAGCGAAGG  GAGATAAGGG
TGGGGCCGTT  TTATAGGATT  TGGGTAGGTA  AAGGAAAATT  ACAGTCAAAG  GGGGTTTGTT
CTCTGGCGGG  CAGGAGTGGG  GGGTCGCAAG  GTGCTCAGTG  GGGGTGCTTT  TTGAGCCAGG
ATGAGCCAGG  AAAAGGACTT  TCACAAGGTA  ATGTCATCAA  TTAAGGCAAG  GACCCGCCAT
TTACACCTCT  TTTGTGGTGG  AATGTCATCA  GTTAAGTTGG  GGCAGGGCAT  ATTCACTTCT
TTTGTGATTC  TTCAGTTACT  TCAGGCCATC  TGGGCGTATA  TGTGCAAGTT  ACAGGGGATG
CGATGGCTTG  GCTTGGGCTC  AGAGGCTTGA  CAGCTACTCT  GGTGGGGCCT  TGGAGAATGT
       SalI
TTGTGTCGAC  ACTCTGTATC  TAGTTAATCT  AGTGGGGACG  TGGAGAACCT  TTGTGTCTAG
CTCAGGGATT  GTAAACGCAC  CAATCAGCGC  CCTGTCAAAA  CAGACCACTC  GGCTCTACCA
ATCAGCAGGA  TGTGGGTGGG  GCCAGATAAG  AGAATAAAAG  CAGGCTGCCC  GAGCCAGCAG
TGGCAACGCG  CACAGGTCCC  TATCCACAAT  ATGGCAGCTT  TGTTCTTTTG  CTGTTTGCGA
TAAATCTTGC  TACTGCTCGC  TTTTTGGGTC  CACACTGCTT  TTATGAGCTG  TAACACTCAC
CACGAAGGTC  TGCAGCTTCA  CTCCTGAAGC  CACTAAGACC  ACGAGCCCAC  CGGGAGGAAT
GAACAACTCC  GGCCGCGCTG  CCTTAAGAGC  TATAACACTC  ACCGCGAAGG  TCTGCAGCTT
```

FIG. 6A

```
CACTCCTCAG CCAGCGAGAC CACGAACCCA CCAGAAGGAA GAAACTGCGA ACACATCTGA
ACATCAGAAG GAACAAACTC CAGATGCACC ACCTTAAGAG CTGTAACACT CACTGCGAGG
GTCCGCGGCT TCCTTCTTGA AGTCAGTGAG ACCAAGCACT CACCAGTTTC GGACACAAGC
CCAGGAGTTT GAGATCAGCC TGGGCAACAT GATGAAATGC CCTCTCTGCA AAAAAAAAA
AAATTACAAA AATTGGCGGA GCATGGTGGT CCGTGCCTGT GGTCCCAGCT ACGCGGGAGG
CTAAAGTGGG AGGATCGCTT GAGCCTGGGA GGTGAAGACT GCAGTGAGCT GTGATTGTAC
CACAGCCCTC TAGGCTGGGG GACAGACTGA GACCCTGTTT CCCCTCCGCA AAAAAATTGA
CAAAAGTGTA ATAAGAGGTG CCTGATATGG CTAGGCGCAG TGGCTCATGC CTGTAATCCC
AGCACTTTGG GAAGCCGAGG CGGGCGGGTC ACCTAAGGTC AGGAGTGTGA GACCAGCCTG
GCCAACATGG AGAAAGCCCA TCTCTTCTAA AAATACAAAA TTAGCCGGCT GTGGGGGCAG
TGGTGGAGCA TGCCTGTAAT CCCAGCTACT CAGGAGGCTG AGGCAGGAGA ATCACTTGAA
CCCAGGAGGC GGCGGTTGCA GTGAGCCGAG ATCGTGCCAT TGCACTCCAC CCACTCCAGC
CTGGGCAACA AGAGCCAAAC TCTGTCTTAA AAAAAAAAA AAAAAGTGCC TGACATATAA
GAGGTGTGCA ATGCAATAGT TGCCAGGCAA CATGTTTAAG AATGTGGAGC TCCTGCCTTC
CATGGTCCTG TTAAAAACCC ACCCTCAAGG CCAGGTGCAG TGGCTCATGC CTATAATCCC
AGCACTTTGG GAGGCCGAGG CGGGTGGATC ACCTGAGGTC AGGAGTTCGA GACCAGCCTG
ACCACCAACA TGGTGAAATC CCACCTCTAC TAAAAATACA AAATTAGATG AGCATGGTGG
TG
```

FIG. 6B

```
               CCTG TAATCCCACC TACTTGGGAG GCTGAGGCAG GAAAATCACT AGAACCAGGG
          AGGCGGAGGT TGTAGTGAGC CGAGATCGTG CCATTGCACT CCAGCCTGAG CAATGAGCGA
          AACTCCATCT CAAAAAAACA ACAACAAAAA CCCACTCTCT ACTCCCAGGG AGCTGGGTAC
          AGAGCTGGGC CACATCAGTG CAAGGTGCTG AGCCACAGAG CTAAGGCGGA GCTGCAGGAC
          CGCGGACCAG ATAACAGTGT GTGAGATCAG TGTGTGAGAT CAGACGTCCC TGCCATTGGT
          GACCACCAGG GGGCCCCCAA GCACCAGAGA TGGCCCCATC CAGTCACCAC ATCCACTTCT
          CATCCAGAGA TGTCTGTTTC TTGGCACGCT GGGGTAAATT AGGACAGAAG GTGACAGTCT
-1457  TGGGTGTGGT CAGTCAGACT GCCCCAGGCA GGCCTTGTGG CCTGTAGAAA ACGTTCAGGC
-1397  CTAGGCCGGG CACGGTGGCT CACGCCTGTA ATCCCAGCAC TTTGGGAGGC CGAGGCGGGT
-1337  GGATCACGAG GTCAGGAGAT CGTGACCATC CTGGCTAACA CGGTGAAACC CCGTCTCTAC
-1277  TAAAAATACA AAAAATTGGC CGGGCATGGT GGCGGGCACC TGTAGTTCCA GCTACTCGGG
-1217  AGGCTGAGGC AGGAGAATGG CGTGAACCCG AGAGGCAGAG TTTGCAGTGA GCCGAGATCG
-1157  CGCCACTGCA CTCCAGCCTG GGCGACAGAG CAAGACTCCA TCTGGAAAAG AAAAAGAAAA
-1097  CGTTCAGGTC TGAGCCAGAG GCCCAGGCTG TAATTCTGTC ACTTACCATG ACCTTGGGCA
-1037  AGGCACTTCC TTCCCTGGCC CAGTTCACGG GGTTGGAATC GACTCCAAGG TCCCTTCCAG
 -977  CATTAACGCT GCATGGTTCT AAGATGAGAA GATGGGGCAG TTTCCCCTCT CTCACCCCAG
 -917  CCCGTGTCCA CTTCAAGGTG AATGACCAGG GAAGTCACGT GTCCAATCC CGCAGTTCCA
 -857  AAGCCCTTGG GGACCCTACT GTCAGGGTCG TGCACGAGGA GGTGAAGGTC AGGTGAGCCA
 -797  ATCGCCTCGA AGGGTCTTGC CTCATTCGGG ACAGACATCC GGTTTCCTCT GGCTCTACCC
 -737  GGATTCTAGG GGCTTTAGCC GAATGAGTCA TGGGGGGCGG GGGGGTTTCT GGGGGAGTTC
                                                            XcmI
 -677  CCAGCTAATC AACTTGGGAC AGGACAGCCT GGAACTTTCG ATGGTGCCTA TCCAAGTG
```

FIG. 7

GENOMIC SEQUENCES FOR PROTEIN PRODUCTION AND DELIVERY

CROSS REFERENCE TO RELATED APPLICATIONS

This application claims the benefit of U.S. Provisional Application Ser. No. 60/084,649, filed May 7, 1998, herein incorporated by reference.

FIELD OF THE INVENTION

This invention relates to genomic DNA.

BACKGROUND OF THE INVENTION

Current approaches to treating disease with therapeutic proteins include both administration of proteins produced in vitro and gene therapy. In vitro production of a protein generally involves the introduction of exogenous DNA coding for the protein of interest into appropriate host cells in culture. Gene therapy methods, on the other hand, involve administering to a patient genetically engineered cells, plasmids, viruses that contain a sequence encoding the therapeutic protein of interest.

Certain therapeutic proteins may also be produced by altering the expression of their endogenous genes in a desired manner with gene targeting techniques. See, e.g., U.S. Pat. Nos. 5,641,670, 5,733,761, and 5,272,071, WO 91/06666, WO 91/06667, and WO 90/11354, all of which are incorporated by reference in their entirety.

SUMMARY OF THE INVENTION

The present invention is based upon the identification and sequencing of genomic DNA 5' to the coding sequence of the human granulocyte colony-stimulating factor ("G-CSF") gene. This DNA can be used, for example, in a DNA construct that alters (e.g., increases) expression of an endogenous G-CSF gene in a mammalian cell upon integration into the genome of the cell via homologous recombination. "Endogenous G-CSF gene" refers to a genomic (i.e., chromosomal) copy of a gene that encodes G-CSF. The construct contains a targeting sequence including or derived from the newly disclosed 5' noncoding sequence, and a transcriptional regulatory sequence. The transcriptional regulatory sequence preferably differs in sequence from the transcriptional regulatory sequence of the endogenous G-CSF gene. The targeting sequence directs the integration of the regulatory sequence into a region within or upstream of the G-CSF-coding sequences of the target gene such that the regulatory sequence becomes operatively linked to the endogenous coding sequence. By "operatively linked" is meant that the regulatory sequence can direct expression of the endogenous G-CSF-coding sequence. The construct may additionally contain a selectable marker gene to facilitate selection of cells that have stably integrated the construct, and/or another coding sequence operatively linked to a promoter.

In one embodiment, the DNA construct contains: (a) a targeting sequence, (b) a regulatory sequence, (c) an exon, and (d) a splice-donor site. The targeting sequence directs the integration of itself and elements (b)–(d) into a region within or upstream of the G-CSF-coding sequences of the target gene. Once integrated, element (b) can direct transcription of elements (c) and (d) and all downstream coding sequences of the endogenous gene. In the construct, the exon is generally 3' of the regulatory sequence, and the splice-donor site is at the 3' end of the exon.

In another embodiment, the DNA construct comprises: (a) a targeting sequence, (b) a regulatory sequence, (c) an exon, (d) a splice-donor site, (e) an intron, and (f) a splice-acceptor site, wherein the targeting sequence directs the integration of itself and elements (b)–(f) such that elements (b)–(f) are within or upstream of the endogenous gene. The regulatory sequences then directs production of a transcript that includes not only elements (c)–(f), but also endogenous G-CSF coding sequences. Preferably, the construct-derived intron and splice-acceptor site are situated in the construct downstream from the splice-donor site.

The targeting sequence is homologous to a pre-selected target site in the genome with which homologous recombination is to occur. It contains at least 20 (e.g., at least 50 or 100) contiguous nucleotides from SEQ ID NO:5, which represents nucleotides −6578 to −364 relative to the translation start site of the human G-CSF gene. By "homologous" is meant that the targeting sequence is identical or sufficiently similar to its genomic target site so that the targeting sequence and target site can undergo homologous recombination. A small percentage of basepair mismatches is acceptable, as long as homologous recombination can occur at a useful frequency. To facilitate homologous recombination, the targeting sequence is preferably at least about 20 (e.g., 50, 100, 250, 400, or 1,000) base pairs ("bp") long. The targeting sequence can also include genomic sequences from outside the region covered by SEQ ID NO:5, so long as it includes at least 20 nucleotides from within this region. For example, additional targeting sequence could be derived from the sequence lying between SEQ ID NO:5 and the endogenous transcription initiation sequence of the G-CSF gene.

Due to polymorphism that may exist at the G-CSF genetic locus, minor variations in the nucleotide composition of any given genomic target site may occur in any given mammalian species. Targeting sequences that correspond to such polymorphic variants of SEQ ID NO:5 (particularly human polymorphic variants) are within the scope of this invention.

Upon homologous recombination, the regulatory sequence of the construct is integrated into a pre-selected region upstream of the coding sequence of a G-CSF gene in a chromosome of a cell. The resulting new transcription unit containing the construct-derived regulatory sequence alters the expression of the target G-CSF gene. The G-CSF protein so produced may be identical in sequence to the G-CSF protein encoded by the unaltered, endogenous gene, or may contain additional, substituted, or fewer amino acid residues as compared to the wild type G-CSF protein, due to changes introduced as a result of homologous recombination.

Altering gene expression encompasses activating (or causing to be expressed) a gene which is normally silent (i.e, essentially unexpressed) in the cell as obtained, increasing or decreasing the expression level of a gene, and changing the regulation pattern of a gene such that the pattern is different from that in the cell as obtained. "Cell as obtained" refers to the cell prior to homologous recombination.

Also within the scope of the invention is a method of using the present DNA construct to alter expression of an endogenous G-CSF gene in a mammalian cell. This method includes the steps of (i) introducing the DNA construct into the mammalian cell, (ii) maintaining the cell under conditions that permit homologous recombination to occur between the construct and a genomic target site homologous to the targeting sequence, to produce a homologously recombinant cell; and (iii) maintaining the homologously recombinant cell under conditions that permit expression of the G-CSF coding sequence under the control of the construct-derived regulatory sequence. At least a part of the genomic target site is 5' to the coding sequence of an endogenous G-CSF gene. That is, the genomic target site can contain coding sequence as well as 5' non-coding sequence.

The invention also features transfected or infected cells in which the construct has undergone homologous recombination with genomic DNA upstream of the endogenous ATG initiation codon in one or both alleles of the endogenous G-CSF gene. Such transfected or infected cells, also called homologously recombinant cells, have an altered G-CSF expression pattern. These cells are particularly useful for in vitro G-CSF production and for delivering G-CSF via gene therapy. Methods of making and using such cells are also embraced by the invention. The cells can be of vertebrate origin such as mammalian (e.g., human, non-human primate, cow, pig, horse, goat, sheep, cat, dog, rabbit, mouse, guinea pig, hamster, or rat) origin.

The invention further relates to a method of producing a mammalian G-CSF protein in vitro or in vivo by introducing the above-described construct into the genome of a host cell via homologous recombination. The homologously recombinant cell is then maintained under conditions that allow transcription, translation, and optionally, secretion of the G-CSF protein.

The invention also features an isolated nucleic acid comprising a sequence of at least 20 (e.g., at least 30, 50, 100, 200, or 1000) contiguous nucleotides of SEQ ID NO:5 or its complement, or of a sequence identical to SEQ ID NO:5 except for polymorphic variations or other minor variations (e.g., less than 5% of the sequence) which does not prevent homologous recombination with the target sequence. In one embodiment, the isolated nucleic acid of the invention includes a contiguous 100 bp block of SEQ ID NO:5. For example, the isolated DNA can contain nucleotides 1 to 100, 101 to 200, 201 to 300, 301 to 400, 401 to 500, 501 to 600, 601 to 700, 701 to 800, 801 to 900, 901 to 1000, 1001 to 1100, 1101 to 1200, 1201 to 1300, 1301 to 1400, 1401 to 1500, 1501 to 1600, 1601 to 1700, 1701 to 1800, 1801 to 1900, 1901 to 2000, 2001 to 2100, 2101 to 2200, 2201 to 2300, 2301 to 2400, 2401 to 2500, 2501 to 2600, 2601 to 2700, 2701 to 2800, 2801 to 2900, 2901 to 3000, 3001 to 3100, 3101 to 3200, 3201 to 3300, 3301 to 3400, 3401 to 3500, 3501 to 3600, 3601 to 3700, 3701 to 3800 3801 to 3900, 3901 to 4000, 4001 to 4100, 4101 to 4200, 4201 to 4300, 4301 to 4400, 4401 to 4500, 4501 to 4600, 4601 to 4700, 4701 to 4800, 4801 to 4900, 4901 to 5000, 5001 to 5100, 5101 to 5200, 5201 to 5300, 5301 to 5400, 5401 to 5500, 5501 to 5600, 5601 to 5700, 5701 to 5800, 5801 to 5900, 5901 to 6000, 6001 to 6100, 6101 to 6200, or 6136 to 6235 of SEQ ID NO:5 or its complement. These blocks of SEQ ID NO:5 and its complement are also useful as targeting sequences in the constructs of the invention.

In the isolated DNA, the SEQ ID NO:5-derived sequence is not linked to a full-length G-CSF-coding sequence, or at least is not linked in the same configuration (i.e., separated by the same noncoding sequence) as occurs in any native genome. The term "isolated DNA", as used herein, thus does not denote a chromosome or large piece of genomic DNA (as might be incorporated into a cosmid or yeast artificial chromosome) that includes not only part or all of SEQ ID NO:5, but also an intact G-CSF coding sequence and all of the sequence which lies between the G-CSF coding sequence and the sequence corresponding to SEQ ID NO:5 as it exists in the genome of a cell. It does include, but is not limited to, a DNA (i) which is incorporated into a plasmid or virus; or (ii) which exists as a separate molecule independent of other sequences, e.g., a fragment produced by polymerase chain reaction ("PCR") or restriction endonuclease treatment. The isolated DNA preferably does not contain a sequence which encodes intact G-CSF precursor (i.e., G-CSF complete with its endogenous secretion signal peptide).

The invention also includes isolated DNA comprising a strand which contains a sequence that is at least 100 (e.g., at least 200, 400, or 1000) nucleotides in length and that hybridizes under either highly stringent or moderately stringent conditions with SEQ ID NO:5, or the complement of SEQ ID NO:5. The sequence is not linked to a G-CSF-coding sequence, or at least is not linked in the same configuration as occurs in any native genome. By moderately stringent conditions is meant hybridization at 50° C. in Church buffer (7% SDS, 0.5% $NaHPO_4$, 1 M EDTA, 1% bovine serum albumin) and washing at 50° C. in 2×SSC. Highly stringent conditions are defined as hybridization at 42° C. in the presence of 50% formamide; a first wash at 65° C. with 2×SSC containing 1% SDS; followed by a second wash at 65° C. with 0.1×SSC.

Also embraced by the invention is isolated DNA comprising a strand which contains a sequence that is at least 100 (e.g., at least 200, 400, or 1000) nucleotides in length and that shares at least 80% (e.g., at least 85%, 90%, 95%, or 98%) sequence identity with a segment of equal length from SEQ ID NO:5 or the complement thereof. The sequence is not linked to a G-CSF-coding sequence, or at least is not linked in the same configuration as occurs in any native genome.

Where a particular polypeptide or nucleic acid molecule is said to have a specific percent identity or conservation to a reference polypeptide or nucleic acid molecule, the percent identity or conservation is determined by the algorithm of Myers and Miller, CABIOS (1989), which is embodied in the ALIGN program (version 2.0), or its equivalent, using a gap length penalty of 12 and a gap penalty of 4 where such parameters are required. All other parameters are set to their default positions. Access to ALIGN is readily available. See, e.g., http://www2.igh.cnrs.fr/bin/align-guess.cgi on the Internet.

The invention also features a method of delivering G-CSF to an animal (e.g., a mammal such as a human, non-human primate, cow, pig, horse, goat, sheep, cat, dog, rabbit, mouse, guinea pig, hamster, or rat) by providing a cell whose endogenous G-CSF gene has been activated as described herein, and implanting the cell in the animal, where the cell secretes G-CSF. Also included in the invention is a method of producing G-CSF by providing a cell whose endogenous G-CSF gene has been activated as described herein, and culturing the cell in vitro under conditions which permit the cell to express and secrete G-CSF.

The isolated DNA of the invention can be used, for example, as a source of an upstream PCR primer for use (when combined with a suitable downstream primer) in obtaining the regulatory and/or coding regions of an endogenous G-CSF gene, or as a hybridization probe for indicating the presence of chromosome 17 in a preparation of human chromosomes. It can also be used, as described below, in a method for altering the expression of an endogenous G-CSF gene in a vertebrate cell.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is a schematic diagram showing the genomic structure of the human G-CSF gene.

FIG. 2 is a schematic diagram showing the human G-CSF genomic regions encompassed by the inserts of plasmids pHGCSF1 and PHGCSF4.

FIG. 3 is a representation of a partial sequence (SEQ ID NO:1) of a human G-CSF gene, including 6,578 nucleotides of the sequence 5' to the ATG initiation codon. Also shown is a partial polypeptide sequence (SEQ ID NO:2) encoded by the coding sequence. Sequences derived from the junction of the genomic insert and the phage arm in the G-CSF/3 phage clone are underlined.

FIG. 5 is a representation of SEQ ID NO:5, a genomic sequence upstream of a human G-CSF transcription start site.

FIG. 6 is a representation of a first targeting sequence (SEQ ID NO:6) used in a construct of the invention.

FIG. 7 is a representation of a second targeting sequence (SEQ ID NO:7) used in a construct of the invention.

DETAILED DESCRIPTION

Figure 4:
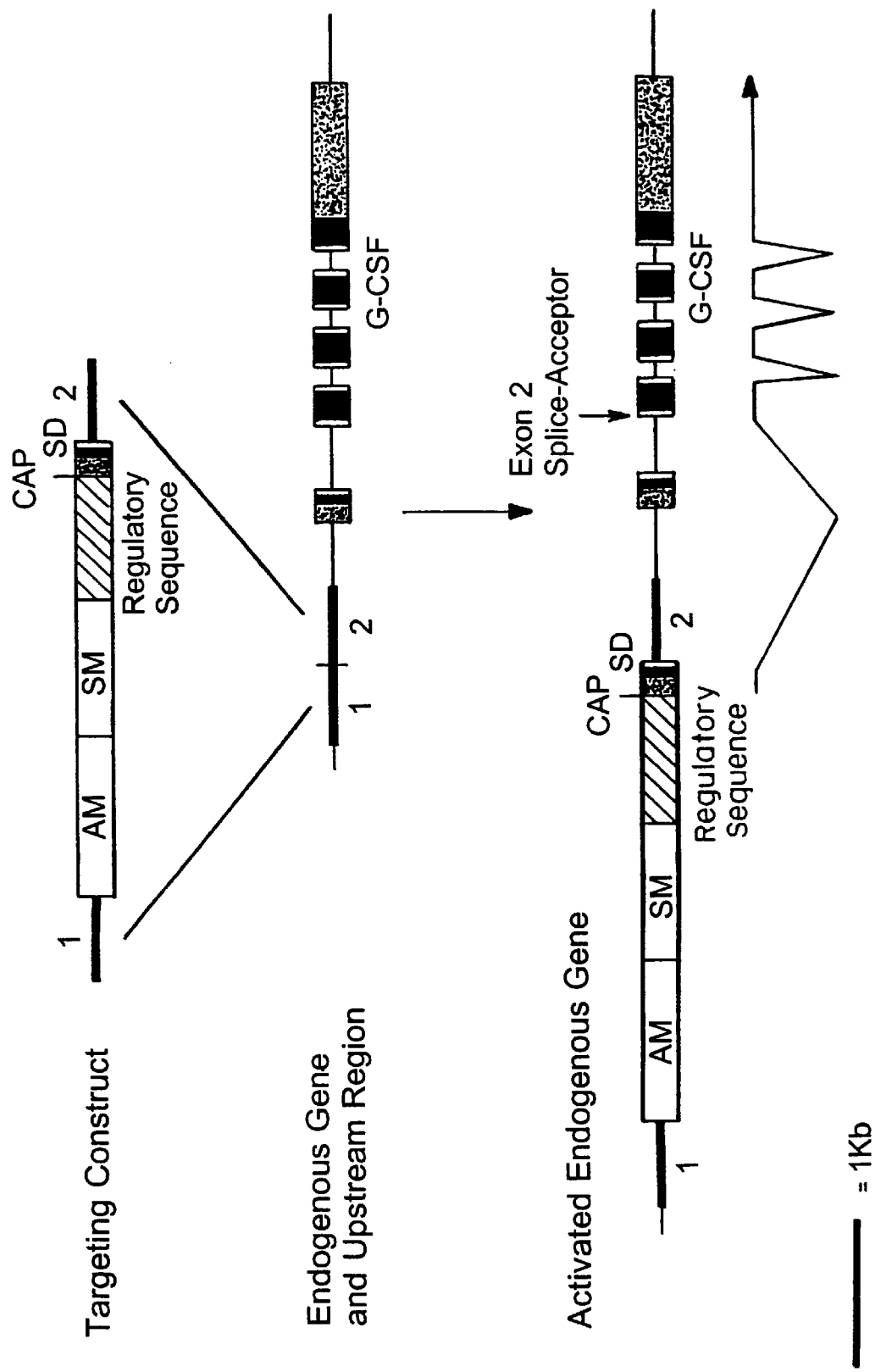
FIG. 4 is a schematic diagram showing a construct of the invention. The construct contains a first targeting sequence (1); an amplifiable marker gene (AM); a selectable marker gene (SM); a regulatory sequence; a CAP site; an exon encoding part of the signal peptide of G-CSF; an unpaired splice-donor site (SD); and a second targeting sequence (2). The black boxes represent coding DNA and the stippled boxes represent transcribed but untranslated sequences.

The present invention is based on the discovery of the nucleotide composition of sequence upstream to the coding sequence of a human G-CSF gene.

G-CSF is a cytokine that stimulates the proliferation and differentiation of hematopoietic progenitor cells committed to the neutrophil/granulocyte lineage. G-CSF is routinely used in the prevention of chemotherapy-induced neutropenia and in association with bone marrow transplantation. Chronic idiopathic and congenital neutropenic disorders also show improvement after G-CSF injection.

The human G-CSF gene encodes a 204 or 207 amino acid precursor protein containing a 30 amino acid signal peptide. The genomic map of the human G-CSF gene is shown in FIG. 1. The map is constructed based on a 2,960 bp published sequence (HUMGCSFG, GenBank accession number X03656) which begins at position −363 relative to the translational start site (unless otherwise specified, all positions referred to herein are relative to the translational start site). The gene contains five exons and four introns, with the first exon encoding 13 ⅔ amino acids of the signal peptide (i.e., the first exon contains 13 codons and the first two nucleotides of the 14th codon encoding the signal peptide).

Sequence 5' to the Human G-CSF Gene

To obtain genomic DNA containing upstream sequence of a G-CSF gene, a human leukocyte genomic library in lambda EMBL3 (Clontech catalog # HL1006d) was screened with a 729 bp oligonucleotide probe generated by PCR. This probe includes G-CSF exons 1 and 2, and was amplified from human genomic DNA using oligonucleotide primers designated 102 and 105, both of which were designed from the available G-CSF genomic DNA sequence (FIG. 1). The 5' end of primer 102 corresponds to position −345, and the primer's sequence is 5'-TATCAGCGGCTCAGCCTTTG-3' (SEQ ID NO:3). The 5' end of primer 105 corresponds to position +384, and the primer's sequence is 5'-CCACCTCACTCACCAGCTTCTC-3' (SEQ ID NO:4).

Approximately 1.5 million recombinant phage were screened with the radiolabelled 729 bp probe. Four independent phage plaques were isolated. One of them, designated clone G-CSF/3, was used for subsequent studies.

A 6.5 kb HindIII-KpnI fragment from phage G-CSF/3 was subcloned into pBluescript II SK+ (Stratagene, La Jolla, Calif) to produce pHGCSF1, which contains the upstream sequences and the entire protein-coding region of the G-CSF gene. An additional upstream subclone, pHGCSF4, was prepared from the 3.3 kb SalI fragment, which overlaps by about 0.4 kb with the insert of pHGCSF1 (FIG. 2).

Figure 3C:
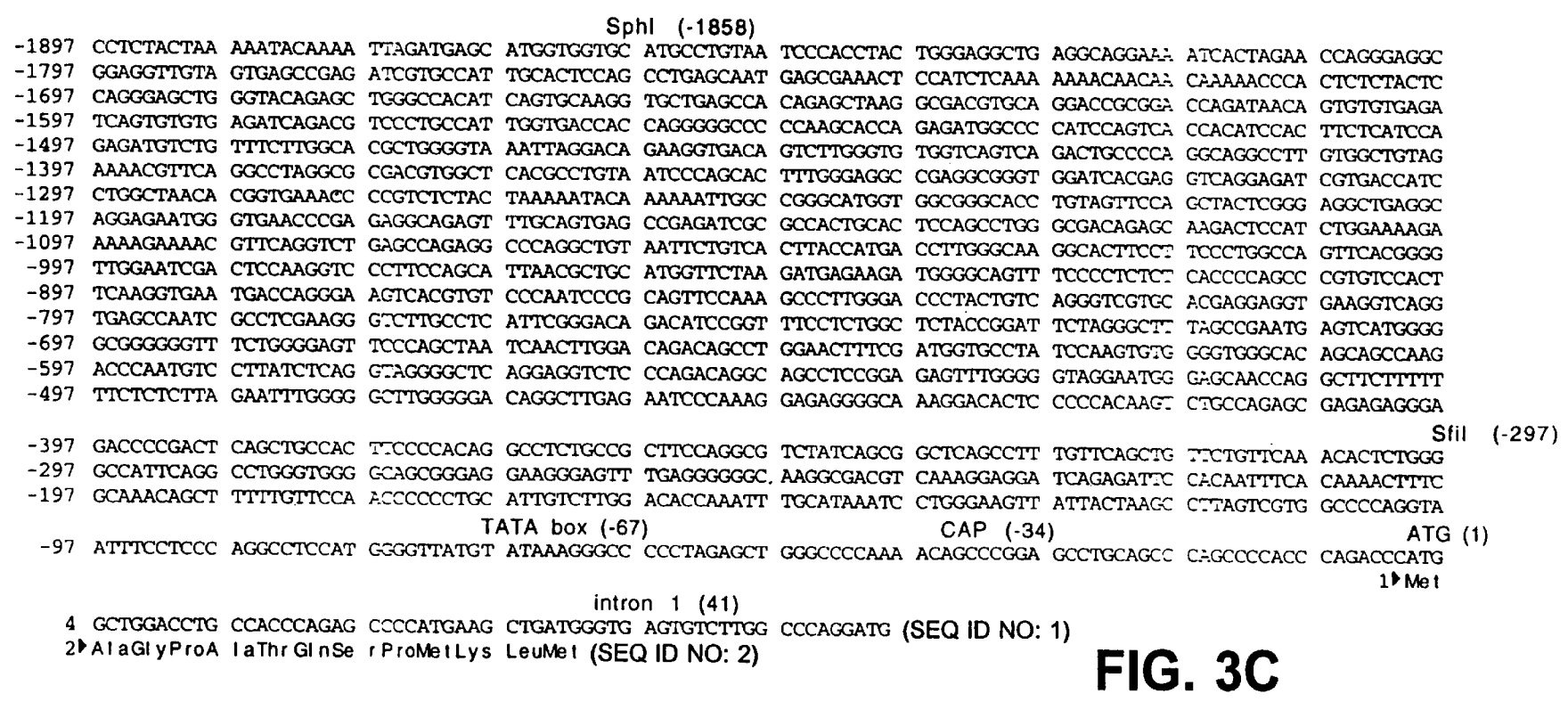

The pHGCSF1 and pHGCSF4 plasmids were sequenced by the Sanger method. The sequence data sets were aligned to obtain the sequence of a 6.6 kb region immediately upstream of the transcription initiation site of the human G-CSF gene, starting at position −6,578. This sequence is part of SEQ ID NO:1, shown in FIG. 3.

The 19 bp (underlined in FIG. 3) at the 5' end of SEQ ID NO:1 are derived from the junction of the genomic insert and the phage arm in the G-CSF/3 phage clone. Therefore, the SalI site in this 19 bp region is not present in the human genome from which the phage library is derived. The sequence between positions −6,578 and −364 (SEQ ID NO:5) is human genomic sequence from a region upstream of the previously-published G-CSF genomic sequence, and has not been reported previously.

To alter the expression of an endogenous G-CSF gene, a DNA fragment containing nucleotides 1470 to 4723 of SEQ ID NO:5 was cloned into plasmid pGG13 upstream of a CMV promoter and a neomycin resistance gene. Nucleotides 1470 to 4723 (SEQ ID NO:6) represent the first targeting sequence as schematically represented in FIG. 4. For the second targeting sequence of FIG. 4, a DNA fragment containing nucleotides 4728 to 5979 (SEQ ID NO:7), relative to the translation start site, of the G-CSF gene sequence was cloned downstream of the CMV promoter and neomycin resistance gene. The pGG13 plasmid was introduced into human fibroblast cells exhibiting little or no G-CSF gene expression to allow homologous recombination with the endogenous G-CSF gene. Cells resistant to G418 after plasmid introduction were screened to identify cells with increased G-CSF gene expression, as would be expected if a homologous recombination event between pGG13 and the genomic DNA took place in the vicinity of the endogenous G-CSF gene.

General Methodologies

Alteration of Endogenous G-CSF Expression

Using the above-described G-CSF upstream sequences, one can alter the expression of an endogenous human G-CSF gene by a method as generally described in U.S. Pat. No. 5,641,670. One strategy is shown in FIG. 4. In this strategy, a targeting construct is designed to include a first targeting sequence homologous to a first target site upstream of the gene, an amplifiable marker gene, a selectable marker gene, a regulatory region, a CAP site, an exon encoding an amino acid sequence which is identical or functionally equivalent to that of the first 13 ⅔ amino acids of the G-CSF signal peptide (i.e., the first exon contains 13 codons and the first two nucleotides of the 14th codon encoding the signal peptide), a splice-donor site, and a second targeting sequence homologous to a second target site downstream of the first target site and terminating either within or upstream of the G-CSF coding sequence. In this strategy, the first and second target sites are immediately adjacent in the chromosome prior to homologous recombination, but such a configuration is not required (see also below). Homologously recombinant cells will produce an mRNA precursor which corresponds to the exogenous exon and splice-donor site, and any sequence between the splice donor site and the transcription termination sequence of the G-CSF gene, including the G-CSF introns, exons, and 3' untranslated region (FIG. 4). Splicing of this transcript results in a mRNA in which the exogenous exon is fused to exon 2 of the endogenous G-CSF gene. Translation of the mRNA produces a precursor G-CSF. The inclusion of a coding exon in the DNA construct allows one to make any desirable modifications to the signal peptide.

Other approaches can also be employed. For example, the first and/or second target sites can be in the first intron of the G-CSF gene. Alternatively, the DNA construct may be designed to include, from 5' to 3', a first targeting sequence, an amplifiable marker gene, a selectable marker gene, a regulatory region, a CAP site, an exon, a splice-donor site, an intron, a splice-acceptor site, and a second targeting sequence. For this strategy, the 5' end of the second target site is preferably less than 60 bp upstream of the normal G-CSF translational initiation site, in order to avoid undesired ATG start codons. A mRNA precursor produced from the homologously recombined locus will include the exogenous exon, the exogenous splice-donor site, the exogenous intron, the exogenous splice-acceptor site, the second targeting sequence, and any sequences between the second targeting sequence and the 3' un-transcribed region of the endogenous gene. Splicing of this transcript will generate a mRNA which can be translated to produce a precursor of human G-CSF, having either the normal G-CSF secretion signal sequence or a genetically engineered secretion signal sequence. The size of the exogenous intron and thus the position of the exogenous regulatory region relative to the coding region of the gene can be varied to optimize the function of the regulatory region.

In any activation strategy, the first and second target sites need not be immediately adjacent or even be near each other. When they are not immediately adjacent to each other, a portion of the G-CSF gene's normal upstream region and/or a portion of the coding region would be deleted upon homologous recombination.

The DNA Construct

The DNA construct of the invention includes at least a targeting sequence and a regulatory sequence. It may additionally contain an exon; or an exon and an unpaired splice-donor site; or an exon, splice donor site, intron, and splice acceptor site. The exon, if present, is 3' of the regulatory sequence, and the unpaired splice-donor site is at the 3' end of the exon. The intron and splice acceptor site, if present, are 3' of the splice donor site. In addition, there can be multiple exons and introns (with appropriate splice donor and acceptor sites) preceding (i.e., 5' to) the exon flanked by the unpaired splice-donor site. The DNA in the construct is referred to as exogenous, since the DNA is not an original part of the genome of a host cell. Exogenous DNA may possess sequences identical to or different from portions of the endogenous genomic DNA present in the cell prior to transfection or infection by viral vector. As used herein, "transfection" means introduction of plasmid into a cell by chemical and physical means such as calcium phosphate or calcium chloride co-precipitation, DEAE-dextran-mediated transfection, lipofection, electroporation, microinjection, microprojectiles, or biolistic-mediated uptake. As used herein "infection" means introduction of viral nucleic acid into a cell by virus infection. The various elements included in the DNA construct of the invention are described in detail below.

The DNA construct can also include cis-acting or trans-acting viral sequences (e.g., packaging signals), thereby enabling delivery of the construct into the nucleus of a cell via infection by a viral vector. Where necessary, the DNA construct can be disengaged from various steps of a virus life cycle, such as integrase-mediated integration in retroviruses or episome maintenance. Disengagement can be accomplished by appropriate deletions or mutations of viral sequences, such as a deletion of the integrase coding region in a retrovirus vector. Additional details regarding the construction and use of viral vectors are found in Robbins et al., Pharmacol. Ther. 80:35–47, 1998; and Gunzburg et al., Mol. Med. Today 1:410–417, 1995, herein incorporated by reference.

Targeting Sequences

Targeting sequences permit homologous recombination of a desired sequence into a selected site in the host genome. Targeting sequences are homologous to (i.e., able to homologously recombine with) their respective target regions in the host genome.

A circular DNA construct can employ a single targeting sequence, or two or more separate targeting sequences. A linear DNA construct may contain two or more separate targeting sequences. The target site to which a given targeting sequence is homologous can reside within an exon and/or intron of the G-CSF gene, upstream of and immediately adjacent to the G-CSF coding region, or upstream of and at a distance from the G-CSF coding region.

The first of the two targeting sequences in the construct (or the entire targeting sequence, if there is only one targeting sequence in the construct) is derived at least in part from the newly disclosed genomic region upstream of the G-CSF-coding sequences. This targeting sequence can contain a portion of SEQ ID NO:1, e.g., at least 20 consecutive nucleotides from the sequence corresponding to positions −6,578 to −364 (SEQ ID NO:5). The second of the two targeting sequences in the construct may target a genomic region upstream of the coding sequence (e.g., also contain a portion of SEQ ID NO:5), or target an exon or intron of the gene.

The targeting sequence(s) may additionally include sequence derived from a previously-disclosed region of the G-CSF gene, including those described herein, as well as a region further upstream which is structurally uncharacterized but can be mapped by one skilled in the art.

Genomic fragments that can be used as targeting sequences can be identified by their ability to hybridize to a probe containing all or a portion of SEQ ID NO:5. Such a probe can be generated by PCR using primers derived from SEQ ID NO:1.

The Regulatory Sequence

The regulatory sequence of the DNA construct can contain one or more promoters (e.g., a constitutive, tissue-specific or inducible promoter), enhancers, scaffold-attachment regions or matrix attachment sites, negative regulatory elements, transcription factor binding sites, or combinations of these elements.

The regulatory sequence can be derived from a eukaryotic (e.g., mammalian) or viral genome. Useful regulatory sequences include, but are not limited to, those that regulate the expression of SV40 early or late genes, cytomegalovirus genes, and adenovirus major late genes. They also include regulatory regions derived from genes encoding mouse metallothionein-I, elongation factor-1α, collagen (e.g., collagen Iα1, collagen Iα2, and collagen IV), actin (e.g., γ-actin), immunoglobulin, HMG-CoA reductase, glyceraldehyde phosphate dehydrogenase, 3-phosphoglyceratekinase, collagenase, stromelysin, fibronectin, vimentin, plasminogen activator inhibitor I, thymosin β4, tissue inhibitors of metalloproteinase, ribosomal proteins, major histocompatibility complex molecules, and human leukocyte antigens.

The regulatory sequence preferably contains a transcription factor binding site such as a TATA Box, CCAAT Box, AP1, Sp1, or a NF-κB binding site.

Marker Genes

If desired, the construct can include a sequence encoding a desired polypeptide, operatively linked to its own promoter. An example of this would be a selectable marker gene, which can be used to facilitate the identification of a targeting event. An amplifiable marker gene can also be used to facilitate selection of cells having co-amplified flanking DNA sequences. Cells containing amplified copies of the amplifiable marker gene can be identified by growth in the presence of an agent that selects for the expression of the amplifiable gene. The activated endogenous G-CSF gene will typically be amplified in tandem with the amplified selectable marker gene. Cells containing multiple copies of the activated endogenous gene may produce very high levels of G-CSF, and are thus useful for in vitro protein production and gene therapy.

The selectable and amplifiable marker genes do not have to lie immediately adjacent to each other. The amplifiable marker gene and selectable marker gene can be the same gene. One or both of the marker genes can be situated in the intron of the DNA construct. Suitable amplifiable marker genes and selectable marker genes are described in U.S. Pat. No. 5,641,670.

The Exogenous Exon

The DNA construct may further contain an exon, i.e., a DNA sequence that is copied into RNA and is present in a mature mRNA molecule. The exon in the construct is referred to herein as an exogenous exon. The exogenous exon can be identical to or differ from the first exon of the human G-CSF gene. Alternatively, the exogenous exon encodes one or more amino acid residues, or partially encodes an amino acid residue (i.e., contains one or two nucleotides of a codon). When the exon contains a coding sequence, the DNA construct should be designed such that, upon transcription and splicing, the reading frame of the resulting mRNA is in-frame with the coding region of the target G-CSF gene. That is, the exogenous exon is spliced to an endogenous exon in a manner that does not change the appropriate reading frame of the portion of the mRNA derived from the endogenous exon.

The inclusion of a coding exon in the targeting construct allows the production of a fusion protein that contains both endogenous G-CSF protein sequence and exogenous protein sequence. Such a hybrid protein may combine the structural, enzymatic, or ligand- or receptor-binding properties from two or more proteins into one polypeptide. For example, the exogenous exon can encode a cell membrane anchor, a signal peptide to improve cellular secretion, a leader sequence, an enzymatic region, a co-factor binding region, or an epitope tag to facilitate purification of the G-CSF hybrid protein produced from the recombined gene locus.

The Splice-Donor Site

The exogenous exon is flanked at its 3' end by a splice-donor site. A splice-donor site is a sequence which directs the splicing of one exon of an RNA transcript to the splice-acceptor site of another exon of the RNA transcript. Typically, the first exon lies 5' of the second exon, and the splice-donor site located at the 3' end of the first exon is paired with a splice-acceptor site on the 5' side of the second exon. Splice-donor sites have a characteristic consensus sequence represented as (A/C)AGGURAGU (where R denotes a purine), with the GU in the fourth and fifth positions being required (Jackson, Nucleic Acids Research 19: 3715–3798, 1991). The first three bases of the splice-donor consensus site are the last three bases of the exon: i.e., they are not spliced out. Splice-donor sites are functionally defined by their ability to effect the appropriate reaction within the mRNA splicing pathway.

By way of example, the splice-donor site can be placed immediately adjacent and 3' to an ATG codon when the presence of one or more intervening nucleotides is not required for the exogenous exon to be in-frame with the second exon of the targeted gene. When the exogenous exon encodes one or more amino acids in-frame with the coding sequence of the targeted gene, the splice-donor site may preferably be placed immediately adjacent to the exogenous coding sequence on its 3' side.

The splice-donor site flanking the exogenous exon is unpaired in the construct, i.e., in the construct itself there is no accompanying splice-acceptor site downstream of the splice-donor site to which the latter can be spliced. Following homologous recombination into the target site upstream of the G-CSF coding sequence, what was the construct's unpaired splice-donor site is functionally paired with an endogenous splice-acceptor site of an endogenous exon of G-CSF. Processing of the transcript produced from the homologously recombined G-CSF gene results in splicing of the exogenous exon to the splice-acceptor site of an endogenous exon.

The construct of the invention can also include a splice acceptor site. This site, in conjunction with a splice donor site, directs the splicing of one exon to another exon. Splice-acceptor sites have a characteristic sequence represented as $(Y)_{10}NYAG$ (SEQ ID NO:8), where Y denotes any pyrimidine and N denotes any nucleotide (Jackson, Nucleic Acids Research 19:3715–3798, 1991).

Introns

The DNA construct may optionally contain an intron. An intron is a sequence of one or more nucleotides lying between a splice-donor site and a splice-acceptor site, and is removed, by splicing, from a precursor RNA molecule in the formation of a mature mRNA molecule.

The CAP Site

The DNA construct can optionally contain a CAP site. A CAP site is a specific transcription start site which is associated with and utilized by the regulatory region. This CAP site is located at a position relative to the regulatory sequence in the construct such that following homologous recombination, the regulatory sequence directs synthesis of a transcript that begins at the CAP site. Alternatively, no CAP site is included in the construct, and the transcriptional apparatus will locate by default an appropriate site in the targeted gene to be utilized as a CAP site.

Additional DNA Elements

The construct may additionally contain sequences which affect the structure or stability of the RNA or protein produced by homologous recombination. Optionally, the DNA construct can include a bacterial origin of replication and bacterial antibiotic resistance markers or other selectable markers, which allow for large-scale plasmid propagation in bacteria or any other suitable cloning/host system.

All of the above-described elements of the DNA construct are operatively linked or functionally placed with respect to each other. That is, upon homologous recombination between the construct and the targeted genomic DNA, the regulatory sequence can direct the production of a primary RNA transcript which initiates at a CAP site (optionally included in the construct) and includes (i) sequence corresponding to the exon and splice-donor site of the construct, if they are present, and (ii) sequence lying between that splice-donor site and the endogenous gene's transcription stop site. The latter sequence may include the G-CSF gene's endogenous regulatory region as well as sequences neighboring that region that are normally not transcribed. In an operatively linked configuration, the splice-donor site of the targeting construct directs a splicing event to a splice-acceptor site flanking one of the exons of the endogenous G-CSF gene, such that the desired protein can be produced from the fully spliced mature transcript. The splice-acceptor site can be endogenous, such that the splicing event is directed to an endogenous exon. In another embodiment where the splice-acceptor site is included in the targeting construct, the splicing event removes the exogenous intron introduced by the targeting construct.

The order of elements in the DNA construct can vary. Where the construct is a circular plasmid or viral vector, the relative order of elements in the resulting structure can be, for example: a targeting sequence, plasmid DNA (comprised of sequences used for the selection and/or replication of the targeting plasmid in a microbial or other suitable host), selectable marker(s), a regulatory sequence, an exon, and an unpaired splice-donor site.

Where the construct is linear, the order can be, for example: a first targeting sequence, a selectable marker gene, a regulatory sequence, an exon, a splice-donor site, and a second targeting sequence; or, in the alternative, a first targeting sequence, a regulatory sequence, an exon, a splice-donor site, a selectable marker gene, and a second targeting sequence. The order of the elements can also be: a first targeting sequence, a selectable marker, a regulatory sequence, an exon, a splice-donor site, an intron, a splice-acceptor site, optionally an internal ribosomal entry site, and a second targeting sequence.

Alternatively, the order can be : a first targeting sequence, a first selectable marker gene, a regulatory sequence, an exon, a splice-donor site, a second targeting sequence, and a second selectable marker gene; or, a first targeting sequence, a regulatory sequence, an exon, a splice-donor site, a first selectable marker gene, a second targeting sequence, and a second selectable marker gene. Recombination between the targeting sequences flanking the first selectable marker with homologous sequences in the host genome results in the targeted integration of the first selectable marker, while the second selectable marker is not integrated. Desired transfected or infected cells are those that are stably transfected or infected with the first, but not second, selectable marker. Such cells can be selected for by growth in a medium containing an agent which selects for expression of the first marker and another agent which selects against the second marker. Transfected or infected cells that have improperly integrated the targeting construct by a mechanism other than homologous recombination would be expected to express the second marker gene and will thereby be killed in the selection medium.

A positively selectable marker is sometimes included in the construct to allow for the selection of cells containing amplified copies of that marker. In this embodiment, the order of construct components can be, for example: a first targeting sequence, an amplifiable positively selectable marker, a second selectable marker (optional), a regulatory sequence, an exon, a splice-donor site, and a second targeting DNA sequence.

The various elements of the construct can be obtained from natural sources (e.g., genomic DNA), or can be produced using genetic engineering techniques or synthetic processes. The regulatory region, CAP site, exon, splice-donor site, intron, and splice acceptor site of the construct can be isolated as a complete unit from, e.g., the human elongation factor-1α (Genbank sequence HUMEF1A) gene or the cytomegalovirus (Genbank sequence HEHCMVP1) immediate early region. These components can also be isolated from separate genes.

Transfection or Infection and Homologous Recombination

The DNA construct of the invention can be introduced into the cell, such as a primary, secondary, or immortalized cell, as a single DNA construct, or as separate DNA sequences which become incorporated into the chromosomal or nuclear DNA of a transfected or infected cell. The DNA can be introduced as a linear, double-stranded (with or without single-stranded regions at one or both ends), single-stranded, or circular molecule. The DNA construct or its RNA equivalent can also be introduced as a viral nucleic acid.

When the construct is introduced into host cells in two separate DNA fragments, the two fragments share DNA sequence homology (overlap) at the 3' end of one fragment and the 5' end of the other, while one carries a first targeting sequence and the other carries a second targeting sequence. Upon introduction into a cell, the two fragments can undergo homologous recombination to form a single molecule with the first and second targeting sequences flanking the region of overlap between the two original fragments. The product molecule is then in a form suitable for homologous recombination with the cellular target sites. More than two fragments can be used, with each of them designed such that they will undergo homologous recombination with each other to ultimately form a product suitable for homologous recombination with the cellular target sites as described above.

The DNA construct of the invention, if not containing a selectable marker itself, can be co-transfected or co-infected with another construct that contains such a marker. A targeting plasmid may be cleaved with a restriction enzyme at one or more sites to create a linear or gapped molecule prior to transfection or infection. The resulting free DNA ends increase the frequency of the desired homologous recombination event. In addition, the free DNA ends may be treated with an exonuclease to create overhanging 5' or 3' single-stranded DNA ends (e.g., at least 30 nucleotides in length, and preferably 100–1000 nucleotides in length) to increase the frequency of the desired homologous recombination event. In this embodiment, homologous recombination between the targeting sequence and the genomic target will result in two copies of the targeting sequences, flanking the elements contained within the introduced plasmid.

The DNA constructs may be transfected into cells (preferably in vitro) by a variety of physical or chemical methods, including electroporation, microinjection, microprojectile bombardment, calcium phosphate precipitation, liposome delivery, or polybrene- or DEAE dextran-mediated transfection.

The transfected or infected cell is maintained under conditions which permit homologous recombination, as described in the art (see, e.g., Capecchi, Science 24:1288–1292, 1989). By "transfected cell" is meant a cell into which (or into an ancestor of which) a DNA molecule has been introduced by a means other than using a viral vector. By "infected cell" is meant a cell into which (or into an ancestor of which) a DNA or RNA molecule has been introduced using a viral vector. Viruses known to be useful as vectors include adenovirus, adeno-associated virus, Herpes virus, mumps virus, poliovirus, lentivirus, retroviruses, Sindbis virus, and vaccinia viruses such as canary pox virus. When the homologously recombinant cell is maintained under conditions sufficient to permit transcription of the DNA, the regulatory region introduced by the DNA construct will alter transcription of the G-CSF gene.

Homologously recombinant cells (i.e., cells that have undergone the desired homologous recombination) can be identified by phenotypic screening or by analyzing the culture supernatant in enzyme-linked immunosorbent assays (ELISA) for G-CSF. Commercial ELISA kits for detecting G-CSF are available from R&D Systems (Minneapolis, Minn.). Homologously recombinant cells can also be identified by Southern and Northern analyses or by polymerase chain reaction (PCR) screening.

As used herein, the term "primary cells" includes (i) cells present in a suspension of cells isolated from a vertebrate tissue source (prior to their being plated, i.e., attached to a tissue culture substrate such as a dish or flask), (ii) cells present in an explant derived from tissue, (iii) cells plated for the first time, and (iv) cell suspensions derived from these plated cells. Primary cells can also be cells as they naturally occur within a human or an animal.

Secondary cells are cells at all subsequent steps in culturing. That is, the first time that plated primary cells are removed from the culture substrate and replated (passaged), they are referred to herein as secondary cells, as are all cells in subsequent passages. Secondary cell strains consist of secondary cells which have been passaged one or more times. Secondary cells typically exhibit a finite number of mean population doublings in culture and the property of contact-inhibited, anchorage-dependent growth (anchorage-dependence does not apply to cells that are propagated in suspension culture). Primary and secondary cells are not immortalized.

Immortalized cells are cell lines (as opposed to cell strains, with the designation "strain" reserved for primary and secondary cells) that exhibit an apparently unlimited lifespan in culture.

Cells selected for transfection or infection can fall into four types or categories: (i) cells which do not, as obtained, make or contain more than trace amounts of the G-CSF protein, (ii) cells which make or contain the protein but in quantities other than those desired (such as, in quantities less than the level which is physiologically normal for the type of cells as obtained, (iii) cells which make the protein at a level which is physiologically normal for the type of cells as obtained, but are to be augmented or enhanced in their content or production, and (iv) cells in which it is desirable to change the pattern of regulation or induction of a gene encoding the protein.

Primary, secondary and immortalized cells to be transfected or infected by the present method can be obtained from a variety of tissues and include all appropriate cell types which can be maintained in culture. For example, suitable primary and secondary cells include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells, and precursors of these somatic cell types. Where the homologously recombinant cells are to be used in gene therapy, primary cells are preferably obtained from the individual to whom the transfected or infected primary or secondary cells are to be administered. However, primary cells can be obtained from a donor (i.e., an individual other than the recipient) of the same species.

Examples of immortalized human cell lines useful for protein production or gene therapy include, but are not limited to, 2780AD ovarian carcinoma cells (Van der Blick et al., Cancer Res., 48:5927–5932, 1988), A549 (American Type Culture Collection ("ATCC") CCL 185), BeWo (ATCC CCL 98), Bowes Melanoma cells (ATCC CRL 9607), CCRF-CEM (ATCC CCL 119), CCRF-HSB-2 (ATCC CCL 120.1), COLO201 (ATCC CCL 224), COLO205 (ATCC CCL 222), COLO 320DM (ATCC CCL 220), COLO 32OHSR (ATCC CCL 220.1), Daudi cells (ATCC CCL 213), Detroit 562 (ATCC CCL 138), HeLa cells and derivatives of HeLa cells (ATCC CCL 2, 2.1 and 2.2), HCT116 (ATCC CCL 247), HL-60 cells (ATCC CCL 240), HT1080 cells (ATCC CCL 121), IMR-32 (ATCC CCL 127), Jurkat cells (ATCC TIB 152), K-562 leukemia cells (ATCC CCL 243), KB carcinoma cells (ATCC CCL 17), KG-1 (ATCC CCL 246), KG-1a (ATCC CCL 246.1), LS123 (ATCC CCL 255), LS174T (ATCC CCL CL-188), LS180 (ATCC CCL CL-187), MCF-7 breast cancer cells (ATCC BTH 22), MOLT-4 cells (ATCC CRL 1582), Namalwa cells (ATCC CRL 1432), NCI-H498 (ATCC CCL 254), NCI-H508 (ATCC CCL 253), NCI-H548 (ATCC CCL 249), NCI-H716 (ATCC CCL 251), NCI-H747 (ATCC CCL 252), NCI-H1688 (ATCC CCL 257), NCI-H2126 (ATCC CCL 256), Raji cells (ATCC CCL 86), RD (ATCC CCL 136), RPMI 2650 (ATCC CCL 30), RPMI 8226 cells (ATCC CCL 155), SNU-C2A (ATCC CCL 250.1), SNU-C2B (ATCC CCL 250), SW-13 (ATCC CCL 105), SW48 (ATCC CCL 231), SW403 (ATCC CCL 230), SW480 (ATCC CCL 227), SW620 (ATCC CCL 227), SW837 (ATCC CCL 235), SW948 (ATCC CCL 237), SW1116 (ATCC CCL 233), SW1417 (ATCC CCL 238), SW1463 (ATCC CCL 234), T84 (ATCC CCL 248), U-937 cells (ATCC CRL 1593), WiDr (ATCC CCL 218), and WI-38VA13 subline 2R4 cells (ATCC CLL 75.1), as well as heterohybridoma cells produced by fusion of human cells and cells of another species. Secondary human fibroblast strains, such as WI-38 (ATCC CCL 75) and MRC-5 (ATCC CCL 171), may be used. In addition, primary, secondary, or immortalized human cells, as well as primary, secondary, or immortalized cells from other species, can be used for in vitro protein production or gene therapy.

G-CSF-expressing Cells

Homologously recombinant cells of the invention express G-CSF at desired levels and are useful for both in vitro production of G-CSF and gene therapy.

Protein Production

Homologously recombinant cells according to this invention can be used for in vitro production of G-CSF. The cells are maintained under conditions, as described in the art, which result in expression of proteins. The G-CSF protein may be purified from cell lysates or cell supernatants. A pharmaceutical composition containing the G-CSF protein can be delivered to a human or an animal by conventional pharmaceutical routes known in the art (e.g., oral, intravenous, intramuscular, intranasal, pulmonary, transmucosal, intradermal, transdermal, rectal, intrathecal, subcutaneous, intraperitoneal, or intralesional). Oral administration may require use of a strategy for protecting the protein from degradation in the gastrointestinal tract: e.g., by encapsulation in polymeric microcapsules.

Gene Therapy

Homologously recombinant cells of the present invention are useful as populations of homologously recombinant cell lines, as populations of homologously recombinant primary or secondary cells, as homologously recombinant clonal cell strains or lines, as homologously recombinant heterogenous cell strains or lines, and as cell mixtures in which at least one representative cell of one of the four preceding categories of homologously recombinant cells is present. Such cells may be used in a delivery system for stimulating the proliferation and differentiation of hematopoietic progenitor cells, or for any other condition treatable with G-CSF. For instance, the cells can be used to prevent chemotherapy-induced neutropenia; to treat patients undergoing, or who have undergone, bone marrow transplantation; or to treat chronic idiopathic and congenital neutropenic disorders.

Homologously recombinant primary cells, clonal cell strains or heterogenous cell strains are administered to an individual in whom the abnormal or undesirable condition is to be treated or prevented, in sufficient quantity and by an appropriate route, to express or make available the protein or exogenous DNA at physiologically relevant levels. A physiologically relevant level is one which either approximates the level at which the product is normally produced in the body or results in improvement of the abnormal or undesirable condition. If the cells are syngeneic with respect to a immunocompetent recipient, the cells can be administered or implanted intravenously, intraarterially, subcutaneously, intraperitoneally, intraomentally, subrenal capsularly, intrathecally, intracranially, or intramuscularly.

If the cells are not syngeneic and the recipient is immunocompetent, the homologously recombinant cells to be administered can be enclosed in one or more semipermeable barrier devices. The permeability properties of the device are such that the cells are prevented from leaving the device upon implantation into a subject, but the therapeutic protein is freely permeable and can leave the barrier device and enter the local space surrounding the implant or enter the systemic circulation. See, e.g., U.S. Pat. Nos. 5,641,670, 5,470,731, 5,620,883, 5,487,737, and co-owned U.S. Patent Application entitled "Delivery of Therapeutic Proteins" (inventors: Justin C. Lamsa and Douglas A. Treco), filed Apr. 16, 1999, all herein incorporated by reference. The barrier device can be implanted at any appropriate site: e.g., intraperitoneally, intrathecally, subcutaneously, intramuscularly, within the kidney capsule, or within the omentum.

Barrier devices are particularly useful and allow homologously recombinant immortalized cells, homologously recombinant cells from another species (homologously recombinant xenogeneic cells), or cells from a nonhistocompatibility-matched donor (homologously recombinant allogeneic cells) to be implanted for treatment of a subject. The devices retain cells in a fixed position in vivo, while protecting the cells from the host's immune system. Barrier devices also allow convenient short-term (i.e., transient) therapy by allowing ready removal of the cells when the treatment regimen is to be halted for any reason. Transfected or infected xenogeneic and allogeneic cells may also be used in the absence of barrier devices for short-term gene therapy. In that case, the G-CSF produced by the cells will be delivered in vivo until the cells are rejected by the host's immune system.

A number of synthetic, semisynthetic, or natural filtration membranes can be used for this purpose, including, but not limited to, cellulose, cellulose acetate, nitrocellulose, polysulfone, polyvinylidene difluoride, polyvinyl chloride polymers and polymers of polyvinyl chloride derivatives. Barrier devices can be utilized to allow primary, secondary, or immortalized cells from another species to be used for gene therapy in humans.

Another type of device useful in the gene therapy of the invention is an implantable collagen matrix in which the cells are embedded. Such a device, which can contain beads to which the cells attach, is described in WO 97/15195, herein incorporated by reference.

The number of cells needed for a given dose or implantation depends on several factors, including the expression level of the protein, the size and condition of the host animal, and the limitations associated with the implantation procedure. Usually the number of cells implanted in an adult human or other similarly-sized animal is in the range of $1 \times 10^4$ to $5 \times 10^{10}$, and preferably $1 \times 10^8$ to $1 \times 10^9$. If desired, they may be implanted at multiple sites in the patient, either at one time or over a period of months or years. The dosage may be repeated as needed.

Other Embodiments

It is to be understood that while the invention has been described in conjunction with the detailed description thereof, the foregoing description is intended to illustrate and not to limit the scope of the invention, which is defined by the scope of the appended claims.

Other aspects, advantages, and modifications are within the scope of the following claims.

What is claimed is:

1. A DNA construct that alters expression of an endogenous G-CSF gene in a mammalian cell upon integration into the genome of the cell via homologous recombination, the construct comprising: (i) a targeting sequence containing at least 20 contiguous nucleotides from SEQ ID NO:5 and (ii) a transcriptional regulatory sequence.

2. The DNA construct of claim 1, wherein the construct further comprises an exon and a splice-donor site.

3. The DNA construct of claim 2, wherein the construct further comprises, downstream from the splice-donor site, an intron and a splice-acceptor site.

4. The DNA construct of claim 1, wherein the construct further comprises a selectable marker gene.

5. The DNA construct of claim 1, wherein the targeting sequence contains at least 50 contiguous nucleotides from SEQ ID NO:5.

6. An isolated nucleic acid comprising at least 20 contiguous nucleotides of SEQ ID NO:5 or its complement, wherein the isolated nucleic acid does not encode full-length G-CSF.

7. The isolated nucleic acid of claim 6, wherein the isolated nucleic acid comprises at least 50 contiguous nucleotides of SEQ ID NO:5 or its complement.

8. The isolated nucleic acid of claim 6, wherein the isolated nucleic acid comprises at least 100 contiguous nucleotides of SEQ ID NO:5 or its complement.

9. The isolated nucleic acid of claim 6, wherein the isolated nucleic acid comprises at least 200 contiguous nucleotides of SEQ ID NO:5 or its complement.

10. The isolated nucleic acid of claim 6, wherein the isolated nucleic acid comprises at least 500 contiguous nucleotides of SEQ ID NO:5 or its complement.

11. The isolated DNA of claim 6, wherein the isolated nucleic acid comprises nucleotides 1470 to 4723 of SEQ ID NO:5, or its complement.

12. The isolated DNA of claim 6, wherein the isolated nucleic acid comprises SEQ ID NO:5 or its complement.

13. An isolated nucleic acid comprising a strand that comprises a nucleotide sequence that (i) is at least 100 nucleotides in length and (ii) hybridizes under highly stringent conditions with SEQ ID NO:5 or the complement thereof.

14. The isolated nucleic acid of claim 13, wherein the nucleotide sequence is at least 200 nucleotides in length.

15. The isolated nucleic acid of claim 13, wherein the nucleotide sequence is at least 400 nucleotides in length.

16. The isolated nucleic acid of claim 13, wherein the nucleotide sequence is at least 1,000 nucleotides in length.

17. An isolated nucleic acid comprising a strand that comprises a nucleotide sequence that (i) is at least 100 nucleotides in length and (ii) shares at least 80% sequence identity with a fragment of SEQ ID NO:5 having the same length as the nucleotide sequence.

18. The isolated nucleic acid of claim 17, wherein the nucleotide sequence is at least 200 nucleotides in length.

19. The isolated nucleic acid of claim 18, wherein the nucleotide sequence is at least 400 nucleotides in length.

20. The isolated nucleic acid of claim 18, wherein the nucleotide sequence is at least 1,000 nucleotides in length.

21. A homologously recombinant cell stably transfected with the DNA construct of claim 1, the DNA construct having undergone homologous recombination with genomic DNA upstream of the ATG initiation codon of an endogenous G-CSF coding sequence.

22. A homologously recombinant cell stably transfected with the DNA construct of claim 2, the DNA construct having undergone homologous recombination with genomic DNA upstream of the ATG initiation codon of an endogenous G-CSF coding sequence.

23. A homologously recombinant cell stably transfected with the DNA construct of claim 3, the DNA construct having undergone homologous recombination with genomic DNA upstream of the ATG initiation codon of an endogenous G-CSF coding sequence.

24. A homologously recombinant cell stably transfected with the DNA construct of claim 4, the DNA construct having undergone homologous recombination with genomic DNA upstream of the ATG initiation codon of an endogenous G-CSF coding sequence.

25. A method of altering expression of an endogenous G-CSF gene in a mammalian cell, the method comprising
introducing the DNA construct of claim 1 into the cell;
maintaining the cell under conditions which permit homologous recombination to occur between the construct and a genomic target site homologous to the targeting sequence, to produce a homologously recombinant cell; and
maintaining the homologously recombinant cell under conditions which permit expression of the G-CSF coding sequence under the control of the transcriptional regulatory sequence.

26. A method of altering expression of an endogenous G-CSF gene in a mammalian cell, the method comprising
introducing the DNA construct of claim 4 into the cell;
maintaining the cell under conditions which permit homologous recombination to occur between the construct and a genomic target site homologous to the targeting sequence, to produce a homologously recombinant cell; and
maintaining the homologously recombinant cell under conditions which permit expression of the G-CSF coding sequence under the control of the transcriptional regulatory sequence.

27. A method of producing G-CSF, comprising
providing the cell of claim 21, and
culturing the cell in vitro under conditions which permit the cell to express and secrete G-CSF.

28. A method of producing G-CSF, comprising
providing the cell of claim 22, and
culturing the cell in vitro under conditions which permit the cell to express and secrete G-CSF.

29. A method of producing G-CSF, comprising
providing the cell of claim 23, and culturing the cell in vitro under conditions which permit the cell to express and secrete G-CSF.

30. A method of producing G-CSF, comprising providing the cell of claim 24, and culturing the cell in vitro under conditions which permit the cell to express and secrete G-CSF.

* * * * *

UNITED STATES PATENT AND TRADEMARK OFFICE
CERTIFICATE OF CORRECTION

PATENT NO. : 6,242,218 B1   Page 1 of 1
DATED : June 5, 2001
INVENTOR(S) : Douglas A. Treco, Michael W. Heartlein and Richard F. Selden It is certified that error appears in the above-identified patent and that said Letters Patent is hereby corrected as shown below:

Title page,
In "OTHER PUBLICATIONS" in the Nishizawa, Mikio et al. reference, change "Responsible to Inducible Expression..." to -- Responsible for Inducible Expression...."

Column 8,
Line 48, unbold the "1" in "SEQ ID NO:1"

Column 12,
Line 19, unbold the "1" in "HUMEF1A"

Column 33,
Line 45, change "SEQ ID NO:5," to -- SEQ ID NO:5 -- .

Signed and Sealed this

Twenty-eighth Day of May, 2002

Attest:

JAMES E. ROGAN
Attesting Officer   Director of the United States Patent and Trademark Office

SEQUENCE LISTING

<160> NUMBER OF SEQ ID NOS: 8

<210> SEQ ID NO 1
<211> LENGTH: 6679
<212> TYPE: DNA
<213> ORGANISM: Homo sapiens

<400> SEQUENCE: 1
gtcgacctgc aggtcaacgg atcacttgag gacagtagtt caagaccagc ctgggcagca    60

-continued

```
tagggagact gtctctacga aaaatcaaaa aattatggcc gggcatggtg gctcacgtct    120
gtaatccctg aactttggga catcaaggca agtggatcac ttgaggtcag gagttcgaga    180
ctagcctggc caacatggtg aaaccctatc tccactaaaa aatacaaaaa ttagccaggc    240
atggtggcag gcacctgtaa tcccggctac tcaggaggct gaggcaggag aatcacttga    300
acccaggagg cggaggttgc agtgagctga gatcacacca ctgcactcca gcctgggtga    360
cagagcaaga ctctatctca aaaaaataa aaaaataaaa aaattagcca ggcatggtag    420
tgcacacctc tagtctcagc tactcaggag gctgaggtgg gaggatcact tgaacctggg    480
gcagtcaagg ctacagtgag ccaagatcat gccactacac tccagcctgg caacagaga    540
gagaccctgt ctctaaaaaa ataataataa taaagaaaaa aacagctctg tttatgtctc    600
ctggtccata catactacta tgtatatagt ttgcaaactc aaagatccag atagtcaatt    660
ttttaggctt gtgggccgta tggtctctgt cacaatcact ctgccctgtc tttctagcac    720
aaaagcagct ataaacaata catacatgaa ttttttatag acatcgagat ttgaatttca    780
tatgattttt acattttata aaataatctt tttaaaaatt ttcccctaac catttaaaag    840
tgtaaaagcc ggccagcgcg ccatcgtcac gcctgtaatt ccagcacttt gggaggctga    900
ggtgggcaga tcacttgaga tcaacagttc gagaccagcc tggccaacat agcaaaaccc    960
catttctact aaaaataaaa aaattagctg ggcatagtgg tgcacacctg tgatcccagc   1020
tacttgggag gctgaggcag gagaatcgct tgaacctggg aagcggaggt tgcagtgagc   1080
caacatcatg ccactgcact ccagcctggg tgacagagtg agacttcgtc tcaacgaaaa   1140
aaaaaagtgt aaaagccatt cctaattcag tgtacatcag tgtacatact caggtctgcg   1200
tactcctgct ctgaggcata cctgagaagt agagttgctt ggtcacagga catacacatt   1260
tccacattaa ctagacacta ccaagttgcc atccaaggag gttttttttt tacaatctac   1320
actcccccca gcaacaaatg agagttactc cagatccttt acaaagatgc tctaagccca   1380
gtaccagatg aaaacaggaa gtgggagggg aagctgccag ccccttctaa ccatgaagaa   1440
atacctggta gagccttctg gatgctggaa ggatgaataa cggggtctc tggagcctgc   1500
cccctgtcag atcactgtga cttctgagcc tccagtccag tctcagcccc atgtgtcatg   1560
gccagtgata atgagccctc actctctgtt tggtctttat tctccccatg tggggctgaa   1620
gtctggattg agccgttatt caagatgtac agctttcttg acaggaaagt agtgtcacag   1680
aaacagcagg ggcttggcaa gatgatctaa ctgcaaatcc tacctggctc agccaccagc   1740
tagttctgtg atcttgaaca agttttttca cttctctgag gccatccctt ggctacaaca   1800
caccagttgg ttgacaggat gaaatgacga agtcccttac acctgtaatc ccagcacttt   1860
gggaggccaa gcgggtgga tggcttgagc ctgagaggtg acagcatgcc ggcagtcctc   1920
acagccctcg ttcgctctcg gcgcctcctc tgcctgggct cccacttcgg tggcacttga   1980
ggagcccttc agcccaccgc tgcactgtgg gagccccttt ctgggctggc caaggccaga   2040
gccggctccc tcagcttgca gggaggtgtg gagggagagg ctcaagcagg aaccggggct   2100
gcgcacggcg cttgcgggcc agctggagtt ccgggtgggc gtgggcttgg cgggccccgc   2160
actcggagca gcgggccagc cctgccaggc cccgggcaat gagaggctta gcacccgggc   2220
cagcggctgc ggagggtgta ctgggtgccc cagcagtgcc agcccgccgg cgctgtgctc   2280
gctcgatttc tcactgggcc ttagcagcct cccgcgggg cagggctcgg gacctgcagc   2340
ccgccatgcc tgagcctccc ctccatgggc tcctgtgcgg cccgagcctc cccgacgagc   2400
```

-continued

```
accacccct gctccacagc gcccagtccc atcgaccacg caagggctga gaagtgcggg    2460
cgcacggcac cgggactggc aggcagctac ccctgcagcc ctggtgcgga atccactggg    2520
tgaagccagc tgggctcctg agtctggtgg agacttggag aacctttatg tctagctcag    2580
ggatcgtaaa tacaccaatc agcaccctgt gtctagctca gggtctgtga atgcaccaat    2640
ccacactctg tatctagcta ctctgatggg gccttggaga acctttatgt ctagctcagg    2700
gattgtaaat acaccaatcg gcactctgta tctagctcaa ggtttgtaaa cacaccaatc    2760
agcaccctgt gtctagctca gggtatgtga atgcaccaat cgacagtctg tatctggcta    2820
ctttcatggg catccgtgtg aagagaccac caaacaggct ttgtgtgagc aataaagctt    2880
ctatcacctg ggtgcaggtg ggctgagtcc gaaaagagag tcagcgaagg gagataaggg    2940
tggggccgtt ttataggatt tgggtaggta aaggaaaatt acagtcaaag ggggtttgtt    3000
ctctggcggg caggagtggg gggtcgcaag gtgctcagtg ggggtgcttt ttgagccagg    3060
atgagccagg aaaaggactt tcacaaggta atgtcatcaa ttaaggcaag gacccgccat    3120
ttacacctct tttgtggtgg aatgtcatca gttaagttgg ggcagggcat attcacttct    3180
tttgtgattc ttcagttact tcaggccatc tgggcgtata tgtgcaagtt acaggggatg    3240
cgatggcttg gcttgggctc agaggcttga cagctactct ggtggggcct tggagaatgt    3300
ttgtgtcgac actctgtatc tagttaatct agtggggacg tggagaacct ttgtgtctag    3360
ctcaggggatt gtaaacgcac caatcagcgc cctgtcaaaa cagaccactc ggctctacca    3420
atcagcagga tgtgggtggg gccagataag agaataaaag caggctgccc gagccagcag    3480
tggcaacgcg cacaggtccc tatccacaat atggcagctt tgttcttttg ctgtttgcga    3540
taaatcttgc tactgctcgc ttttttgggtc cacactgctt ttatgagctg taacactcac    3600
cacgaaggtc tgcagcttca ctcctgaagc cactaagacc acgagcccac cgggaggaat    3660
gaacaactcc ggccgcgctg ccttaagagc tataacactc accgcgaagg tctgcagctt    3720
cactcctcag ccagcgagac cacgaaccca ccagaaggaa gaaactgcga acacatctga    3780
acatcagaag gaacaaactc cagatgcacc accttaagag ctgtaacact cactgcgagg    3840
gtccgcggct tccttcttga agtcagtgag accaagcact caccagtttc ggacacaagc    3900
ccaggagttt gagatcagcc tgggcaacat gatgaaatgc cctctctgca aaaaaaaaa    3960
aaattacaaa aattggcgga gcatggtggt ccgtgcctgt ggtcccagct acgcgggagg    4020
ctaaagtggg aggatcgctt gagcctggga ggtgaagact gcagtgagct gtgattgtac    4080
cacagccctc taggctgggg gacagactga gaccctgttt cccctccgca aaaaaattga    4140
caaaagtgta ataagaggtg cctgatatgg ctaggcgcag tggctcatgc ctgtaatccc    4200
agcactttgg gaagccgagg cgggcgggtc acctaaggtc aggagtgtga gaccagcctg    4260
gccaacatga agaagcccca tctcttctaa aaatacaaaa ttagccggct gtgggggcag    4320
tggtggagca tgcctgtaat cccagctact caggaggctg aggcaggaga atcacttgaa    4380
cccaggaggc ggcggttgca gtgagccgag atcgtgccat gcactccac ccactccagc    4440
ctgggcaaca agagccaaac tctgtcttaa aaaaaaaaa aaaagtgcc tgacatataa    4500
gaggtgtgca atgcaaatagt tgccaggcaa catgtttaag aatgtggagc tcctgccttc    4560
catggtcctg ttaaaacccc accctcaagg ccaggtgcag tggctcatgc ctataatccc    4620
agcactttgg gaggccgagg cgggtggatc acctgaggtc aggagttcga gaccagcctg    4680
accaccaaca tggtgaaatc ccacctctac taaaaataca aaattagatg agcatggtgg    4740
tgcatgcctg taatcccacc tacttgggag gctgaggcag gaaaatcact agaaccaggg    4800
```

-continued

```
aggcggaggt tgtagtgagc cgagatcgtg ccattgcact ccagcctgag caatgagcga   4860
aactccatct caaaaaaaca acaacaaaaa cccactctct actcccaggg agctgggtac   4920
agagctgggc cacatcagtg caaggtgctg agccacagag ctaaggcgga gctgcaggac   4980
cgcggaccag ataacagtgt gtgagatcag tgtgtgagat cagacgtccc tgccattggt   5040
gaccaccagg gggcccccaa gcaccagaga tggccccatc cagtcaccac atccacttct   5100
catccagaga tgtctgtttc ttggcacgct ggggtaaatt aggacagaag gtgacagtct   5160
tgggtgtggt cagtcagact gccccaggca ggccttgtgg cctgtagaaa acgttcaggc   5220
ctaggccggg cacggtggct cacgcctgta atcccagcac tttgggaggc cgaggcgggt   5280
ggatcacgag gtcaggagat cgtgaccatc ctggctaaca cggtgaaacc ccgtctctac   5340
taaaaataca aaaaattggc cgggcatggt ggcgggcacc tgtagttcca gctactcggg   5400
aggctgaggc aggagaatgg cgtgaacccg agaggcagag tttgcagtga gccgagatcg   5460
cgccactgca ctccagcctg ggcgacagag caagactcca tctggaaaag aaaaagaaaa   5520
cgttcaggtc tgagccagag gcccaggctg taattctgtc acttaccatg accttgggca   5580
aggcacttcc ttccctggcc cagttcacgg ggttggaatc gactccaagg tcccttccag   5640
cattaacgct gcatggttct aagatgagaa gatggggcag tttcccctct ctcaccccag   5700
cccgtgtcca cttcaaggtg aatgaccagg gaagtcacgt gtcccaatcc cgcagttcca   5760
aagcccttgg ggaccctact gtcagggtcg tgcacgagga ggtgaaggtc aggtgagcca   5820
atcgcctcga agggtcttgc ctcattcggg acagacatcc ggtttcctct ggctctaccg   5880
ggattctagg ggctttagcc gaatgagtca tgggggggcgg gggggtttct gggggagttc   5940
ccagctaatc aacttgggac aggacagcct ggaactttcg atggtgccta tccaagtgtg   6000
gggtgggcac agcagccaag acccaatgtc cttatctcag gtaggggctc aggaggtctc   6060
ccagacaggc agcctccgga gagtttgggg gtaggaatgg gagcaaccag gcttcttttt   6120
ttctctctta gaatttgggg gcttggggga caggcttgag aatcccaaag gagaggggca   6180
aaggacactc ccccacaagt ctgccagagc gagagaggga gaccccgact cagctgccac   6240
ttccccacag gcctctgccg cttccaggcg tctatcagcg gctcagcctt tgttcagctg   6300
ttctgttcaa acactctggg gccattcagg cctgggtggg gcagcgggag gaagggagtt   6360
tgaggggggc aaggcgacgt caaaggagga tcagagattc cacaatttca caaaactttc   6420
gcaaacagct ttttgttcca accccctgc attgtcttgg acaccaaatt tgcataaatc   6480
ctgggaagtt attactaagc cttagtcgtg gccccaggta atttcctccc aggcctccat   6540
ggggttatgt ataaagggcc ccctagagct gggccccaaa acagcccgga gcctgcagcc   6600
cagccccacc cagacccatg gctggacctg ccacccagag ccccatgaag ctgatgggtg   6660
agtgtcttgg cccaggatg                                               6679
```

<210> SEQ ID NO 2
<211> LENGTH: 13
<212> TYPE: PRT
<213> ORGANISM: Homo sapiens

<400> SEQUENCE: 2

```
Met Ala Gly Pro Ala Thr Gln Ser Pro Met Lys Leu Met
  1               5                  10
```

<210> SEQ ID NO 3
<211> LENGTH: 20
```
<212> TYPE: DNA
<213> ORGANISM: Homo sapiens

<400> SEQUENCE: 3
tatcagcggc tcagcctttg                                                 20

<210> SEQ ID NO 4
<211> LENGTH: 22
<212> TYPE: DNA
<213> ORGANISM: Homo sapiens

<400> SEQUENCE: 4
ccacctcact caccagcttc tc                                              22

<210> SEQ ID NO 5
<211> LENGTH: 6235
<212> TYPE: DNA
<213> ORGANISM: Homo sapiens

<400> SEQUENCE: 5
gatcacttga ggacagtagt tcaagaccag cctgggcagc ataggagac tgtctctacg       60 aaaaatcaaa aaattatggc cgggcatggt ggctcacgtc tgtaatccct gaactttggg    120
acatcaaggc aagtggatca cttgaggtca ggagttcgag actagcctgg ccaacatggt    180
gaaaccctat ctccactaaa aatacaaaa attagccagg catggtggca ggcacctgta     240
atcccggcta ctcaggaggc tgaggcagga gaatcacttg aacccaggag gcggaggttg    300
cagtgagctg agatcacacc actgcactcc agcctgggtg acagagcaag actctatctc    360
aaaaaaaata aaaaaataaa aaattagcc aggcatggta gtgcacacct ctagtctcag     420
ctactcagga ggctgaggtg ggaggatcac ttgaacctgg ggcagtcaag gctacagtga    480
gccaagatca tgccactaca ctccagcctg gcaacagag agagaccctg tctctaaaaa     540
aataataata ataaagaaaa aaacagctct gtttatgtct cctggtccat acatactact    600
atgtatatag tttgcaaact caaagatcca gatagtcaat tttttaggct tgtgggccgt    660
atggtctctg tcacaatcac tctgccctgt ctttctagca caaaagcagc tataaacaat    720
acatacatga atttttata gacatcgaga tttgaatttc atatgatttt tacattttat    780
aaaataatct ttttaaaaat tttcccctaa ccatttaaaa gtgtaaaagc cggccagcgc    840
gccatcgtca cgcctgtaat tccagcactt tgggaggctg aggtgggcag atcacttgag    900
atcaacagtt cgagaccagc ctggccaaca tagcaaaacc ccatttctac taaaaataaa    960
aaaattagct gggcatagtg gtgcacacct gtgatcccag ctacttggga ggctgaggca   1020
ggagaatcgc ttgaacctgg gaagcggagg ttgcagtgag ccaacatcat gccactgcac   1080
tccagcctgg gtgacagagt gagacttcgt ctcaacgaaa aaaaaagtg taaaagccat   1140 tcctaattca gtgtacatca gtgtacatac tcaggtctgc gtactcctgc tctgaggcat    1200
acctgagaag tagagttgct tggtcacagg acatacacat ttccacatta actagacact    1260
accaagttgc catccaagga ggttttttttt ttacaatcta cactcccccc agcaacaaat   1320
gagagttact ccagatcctt tacaaagatg ctctaagccc agtaccagat gaaaacagga    1380
agtgggaggg gaagctgcca gcccttcta accatgaaga aatacctggt agagccttct    1440
ggatgctgga aggatgaata acgggggtct ctggagcctg cccctgtca gatcactgtg     1500 acttctgagc ctccagtcca gtctcagccc catgtgtcat ggccagtgat aatgagccct    1560
cactctctgt ttggtctttta ttctccccat gtggggctga agtctggatt gagccgttat   1620
```

-continued

```
tcaagatgta cagctttctt gacaggaaag tagtgtcaca gaaacagcag gggcttggca    1680
agatgatcta actgcaaatc ctacctggct cagccaccag ctagttctgt gatcttgaac    1740
aagttttttc acttctctga ggccatccct tggctacaac acaccagttg gttgacagga    1800
tgaaatgacg aagtccctta cacctgtaat cccagcactt tgggaggcca aggcgggtgg    1860
atggcttgag cctgagaggt gacagcatgc cggcagtcct cacagccctc gttcgctctc    1920
ggcgcctcct ctgcctgggc tcccacttcg gtggcacttg aggagcccct cagcccaccg    1980
ctgcactgtg ggagcccctt ctgggctgg ccaaggccag agccggctcc ctcagcttgc     2040
agggaggtgt ggagggagag gctcaagcag gaaccggggc tgcgcacggc gcttgcgggc    2100
cagctggagt tccgggtggg cgtgggcttg gcgggccccg cactcggagc agcgggccag    2160
ccctgccagg ccccgggcaa tgagaggctt agcacccggg ccagcggctg cggagggtgt    2220
actgggtgcc ccagcagtgc cagcccgccg gcgctgtgct cgctcgattt ctcactgggc    2280
cttagcagcc ttcccgcggg gcagggctcg ggacctgcag cccgccatgc ctgagcctcc    2340
cctccatggg ctcctgtgcg gcccgagcct cccgacgag caccacccc tgctccacag      2400
cgcccagtcc catcgaccac gcaagggctg agaagtgcgg gcgcacggca ccgggactgg    2460
caggcagcta cccctgcagc cctggtgcgg aatccactgg gtgaagccag ctgggctcct    2520
gagtctggtg gagacttgga gaacctttat gtctagctca gggatcgtaa atacaccaat    2580
cagcaccctg tgtctagctc agggtctgtg aatgcaccaa tccacactct gtatctagct    2640
actctgatgg ggccttggag aacctttatg tctagctcag ggattgtaaa tacaccaatc    2700
ggcactctgt atctagctca aggtttgtaa acacaccaat cagcaccctg tgtctagctc    2760
agggtatgtg aatgcaccaa tcgacagtct gtatctggct actttcatgg gcatccgtgt    2820
gaagagacca ccaaacaggc tttgtgtgag caataaagct tctatcacct gggtgcaggt    2880
gggctgagtc cgaaaagaga gtcagcgaag ggagataagg gtgggccgt tttataggat      2940
ttgggtaggt aaaggaaaat tacagtcaaa ggggtttgt tctctggcgg gcaggagtgg      3000
ggggtcgcaa ggtgctcagt gggggtgctt tttgagccag gatgagccag gaaaaggact    3060
tcacaaggt aatgtcatca attaaggcaa ggacccgcca tttacacctc ttttgtggtg     3120
gaatgtcatc agttaagttg gggcagggca tattcacttc ttttgtgatt cttcagttac    3180
ttcaggccat ctgggcgtat atgtgcaagt tacaggggat gcgatggctt ggcttgggct    3240
cagaggcttg acagctactc tggtggggcc ttggagaatg tttgtgtcga cactctgtat    3300
ctagttaatc tagtggggac gtggagaacc tttgtgtcta gctcagggat tgtaaacgca    3360
ccaatcagcg ccctgtcaaa acagaccact cggctctacc aatcagcagg atgtgggtgg    3420
ggccagataa gagaataaaa gcaggctgcc cgagccagca gtggcaacgc gcacaggtcc    3480
ctatccacaa tatggcagct ttgttctttt gctgtttgcg ataaatcttg ctactgctcg    3540
ctttttgggt ccacactgct tttatgagct gtaacactca ccacgaaggt ctgcagcttc    3600
actcctgaag ccactaagac cacgagccca ccggaggaa tgaacaactc cggccgcgct     3660
gccttaagag ctataacact caccgcgaag gtctgcagct tcactcctca gccagcgaga    3720
ccacgaaccc accagaagga agaaactgcg aacacatctg aacatcagaa ggaacaaact    3780
ccagatgcac caccttaaga gctgtaacac tcactgcgag ggtccgcggc ttccttcttg    3840
aagtcagtga gaccaagcac tcaccagttt cggacacaag cccaggagtt tgagatcagc    3900
ctggcaaca tgatgaaatg ccctctctgc aaaaaaaaaa aaaattacaa aaattggcgg     3960
agcatggtgg tccgtgcctg tggtcccagc tacgcgggag gctaaagtgg gaggatcgct    4020
```

```
tgagcctggg aggtgaagac tgcagtgagc tgtgattgta ccacagccct ctaggctggg    4080
ggacagactg agaccctgtt tcccctccgc aaaaaaattg acaaaagtgt aataagaggt    4140
gcctgatatg gctaggcgca gtggctcatg cctgtaatcc cagcactttg ggaagccgag    4200
gcgggcgggt cacctaaggt caggagtgtg agaccagcct ggccaacatg gagaaagccc    4260
atctcttcta aaaatacaaa attagccggc gtgggggca gtggtggagc atgcctgtaa    4320
tcccagctac tcaggaggct gaggcaggag aatcacttga acccaggagg cggcggttgc    4380
agtgagccga gatcgtgcca ttgcactcca cccactccag cctgggcaac aagagccaaa    4440
ctctgtctta aaaaaaaaa aaaaagtgc ctgacatata agaggtgtgc aatgcaatag    4500
ttgccaggca acatgtttaa gaatgtggag ctcctgcctt ccatggtcct gttaaaaacc    4560
caccctcaag gccaggtgca gtggctcatg cctataatcc cagcactttg ggaggccgag    4620
gcgggtggat cacctgaggt caggagttcg agaccagcct gaccaccaac atggtgaaat    4680
cccacctcta ctaaaaatac aaaattagat gagcatggtg gtgcatgcct gtaatcccac    4740
ctacttggga ggctgaggca ggaaaatcac tagaaccagg gaggcggagg ttgtagtgag    4800
ccgagatcgt gccattgcac tccagcctga gcaatgagcg aaactccatc tcaaaaaaac    4860
aacaacaaaa acccactctc tactcccagg gagctgggta cagagctggg ccacatcagt    4920
gcaaggtgct gagccacaga gctaaggcgg agctgcagga ccgcggacca gataacagtg    4980
tgtgagatca gtgtgtgaga tcagacgtcc ctgccattgg tgaccaccag ggggccccca    5040
agcaccagag atggccccat ccagtcacca catccacttc tcatccagag atgtctgttt    5100
cttggcacgc tggggtaaat taggacagaa ggtgacagtc ttgggtgtgg tcagtcagac    5160
tgccccaggc aggccttgtg gcctgtagaa aacgttcagg cctaggccgg gcacggtggc    5220
tcacgcctgt aatcccagca ctttgggagg ccgaggcggg tggatcacga ggtcaggaga    5280
tcgtgaccat cctggctaac acggtgaaac cccgtctcta ctaaaaatac aaaaaattgg    5340
ccgggcatgg tggcgggcac ctgtagttcc agctactcgg gaggctgagg caggagaatg    5400
gcgtgaaccc gagaggcaga gtttgcagtg agccgagatc gcgccactgc actccagcct    5460
gggcgacaga gcaagactcc atctggaaaa gaaaaagaaa acgttcaggt ctgagccaga    5520
ggcccaggct gtaattctgt cacttaccat gaccttgggc aaggcacttc cttccctggc    5580
ccagttcacg gggttggaat cgactccaag gtcccttcca gcattaacgc tgcatggttc    5640
taagatgaga agatggggca gtttcccctc tctcacccca gcccgtgtcc acttcaaggt    5700
gaatgaccag ggaagtcacg tgtcccaatc ccgcagttcc aaagcccttg ggaccctac    5760 tgtcagggtc gtgcacgagg aggtgaaggt caggtgagcc aatcgcctcg aagggtcttg    5820
cctcattcgg gacagacatc cggtttcctc tggctctacc gggattctag ggctttagc    5880 cgaatgagtc atgggggcg ggggggtttc tggggagtt cccagctaat caacttggga    5940
caggacagcc tggaactttc gatggtgcct atccaagtgt ggggtgggca cagcagccaa    6000
gacccaatgt ccttatctca ggtagggct caggaggtct cccagacagg cagcctccgg    6060
agagtttggg ggtaggaatg ggagcaacca ggcttctttt tttctctctt agaatttggg    6120
ggcttggggg acaggcttga gaatcccaaa ggagaggggc aaaggacact cccccacaag    6180
tctgccagag cgagagaggg agaccccgac tcagctgcca cttccccaca ggcct         6235
```

<210> SEQ ID NO 6
<211> LENGTH: 2834
<212> TYPE: DNA

<213> ORGANISM: Homo sapiens

<400> SEQUENCE: 6

| | | | | |
|---|---|---|---|---|
| ccggcagtcc | tcacagccct | cgttcgctct | cggcgcctcc | tctgcctggg | ctcccacttc | 60 |
| ggtggcactt | gaggagccct | tcagcccacc | gctgcactgt | gggagcccct | ttctgggctg | 120 |
| gccaaggcca | gagccggctc | cctcagcttg | caggaggtg | tggagggaga | ggctcaagca | 180 |
| ggaaccgggg | ctgcgcacgg | cgcttgcggg | ccagctggag | ttccgggtgg | gcgtgggctt | 240 |
| ggcgggcccc | gcactcggag | cagcgggcca | gccctgccag | gccccgggca | atgagaggct | 300 |
| tagcacccgg | gccagcggct | gcggagggtg | tactgggtgc | cccagcagtg | ccagcccgcc | 360 |
| ggcgctgtgc | tcgctcgatt | tctcactggg | ccttagcagc | cttcccgcgg | ggcagggctc | 420 |
| gggacctgca | gcccgccatg | cctgagcctc | ccctccatgg | gctcctgtgc | ggcccgagcc | 480 |
| tccccgacga | gcaccacccc | ctgctccaca | gcgcccagtc | ccatcgacca | cgcaagggct | 540 |
| gagaagtgcg | ggcgcacggc | accgggactg | gcaggcagct | acccctgcag | ccctggtgcg | 600 |
| gaatccactg | ggtgaagcca | gctggctcc | tgagtctggt | ggagacttgg | agaaccttta | 660 |
| tgtctagctc | agggatcgta | aatacaccaa | tcagcaccct | gtgtctagct | cagggtctgt | 720 |
| gaatgcacca | atccacactc | tgtatctagc | tactctgatg | gggccttgga | gaaccttat | 780 |
| gtctagctca | gggattgtaa | atacaccaat | cggcactctg | tatctagctc | aaggtttgta | 840 |
| aacacaccaa | tcagcaccct | gtgtctagct | cagggtatgt | gaatgcacca | atcgacagtc | 900 |
| tgtatctggc | tactttcatg | ggcatccgtg | tgaagagacc | accaaacagg | ctttgtgtga | 960 |
| gcaataaagc | ttctatcacc | tgggtgcagg | tgggctgagt | ccgaaaagag | agtcagcgaa | 1020 |
| gggagataag | ggtggggccg | ttttatagga | tttgggtagg | taaaggaaaa | ttacagtcaa | 1080 |
| aggggtttg | ttctctggcg | ggcaggagtg | ggggtcgca | aggtgctcag | tgggggtgct | 1140 |
| ttttgagcca | ggatgagcca | ggaaaaggac | tttcacaagg | taatgtcatc | aattaaggca | 1200 |
| aggacccgcc | atttacacct | cttttgtggt | ggaatgtcat | cagttaagtt | ggggcagggc | 1260 |
| atattcactt | cttttgtgat | tcttcagtta | cttcaggcca | tctgggcgta | tatgtgcaag | 1320 |
| ttacaggga | tgcgatggct | tggcttgggc | tcagaggctt | gacagctact | ctggtggggc | 1380 |
| cttggagaat | gtttgtgtcg | acactctgta | tctagttaat | ctagtgggga | cgtggagaac | 1440 |
| ctttgtgtct | agctcaggga | ttgtaaacgc | accaatcagc | gccctgtcaa | acagaccac | 1500 |
| tcggctctac | caatcagcag | gatgtgggtg | gggccagata | agagaataaa | agcaggctgc | 1560 |
| ccgagccagc | agtggcaacg | cgcacaggtc | cctatccaca | atatggcagc | tttgttcttt | 1620 |
| tgctgtttgc | gataaatctt | gctactgctc | gcttttttggg | tccacactgc | ttttatgagc | 1680 |
| tgtaacactc | accacgaagg | tctgcagctt | cactcctgaa | gccactaaga | ccacgagccc | 1740 |
| accgggagga | atgaacaact | ccggccgcgc | tgccttaaga | gctataacac | tcaccgcgaa | 1800 |
| ggtctgcagc | ttcactcctc | agccagcgag | accacgaacc | caccagaagg | aagaaactgc | 1860 |
| gaacacatct | gaacatcaga | aggaacaaac | tccagatgca | ccaccttaag | agctgtaaca | 1920 |
| ctcactgcga | gggtccgcgg | cttccttctt | gaagtcagtg | agaccaagca | ctcaccagtt | 1980 |
| tcggacacaa | gcccaggagt | ttgagatcag | cctgggcaac | atgatgaaat | gccctctctg | 2040 |
| caaaaaaaaa | aaaaattaca | aaaattggcg | gagcatggtg | gtccgtgcct | gtggtcccag | 2100 |
| ctacgcggga | ggctaaagtg | ggaggatcgc | ttgagcctgg | gaggtgaaga | ctgcagtgag | 2160 |
| ctgtgattgt | accacagccc | tctaggctgg | gggacagact | gagaccctgt | ttcccctccg | 2220 |
| caaaaaaatt | gacaaaagtg | taataagagg | tgcctgatat | ggctaggcgc | agtggctcat | 2280 |

```
gcctgtaatc ccagcacttt gggaagccga ggcgggcggg tcacctaagg tcaggagtgt      2340
gagaccagcc tggccaacat ggagaaagcc catctcttct aaaaatacaa aattagccgg      2400
ctgtgggggc agtggtggag catgcctgta atcccagcta ctcaggaggc tgaggcagga      2460
gaatcacttg aacccaggag gcggcggttg cagtgagccg agatcgtgcc attgcactcc      2520
acccactcca gcctgggcaa caagagccaa actctgtctt aaaaaaaaaa aaaaaagtg      2580 cctgacatat aagaggtgtg caatgcaata gttgccaggc aacatgttta agaatgtgga      2640
gctcctgcct tccatggtcc tgttaaaaac ccaccctcaa ggccaggtgc agtggctcat      2700
gcctataatc ccagcacttt gggaggccga ggcgggtgga tcacctgagg tcaggagttc      2760
gagaccagcc tgaccaccaa catggtgaaa tcccacctct actaaaaata caaaattaga      2820
tgagcatggt ggtg                                                       2834
```

<210> SEQ ID NO 7
<211> LENGTH: 1252
<212> TYPE: DNA
<213> ORGANISM: Homo sapiens

<400> SEQUENCE: 7

```
cctgtaatcc cacctacttg ggaggctgag gcaggaaaat cactagaacc agggaggcgg       60
aggttgtagt gagccgagat cgtgccattg cactccagcc tgagcaatga gcgaaactcc      120
atctcaaaaa aacaacaaca aaacccact ctctactccc agggagctgg gtacagagct      180
gggccacatc agtgcaaggt gctgagccac agagctaagg cggagctgca ggaccgcgga      240
ccagataaca gtgtgtgaga tcagtgtgtg agatcagacg tccctgccat tggtgaccac      300 caggggccc ccaagcacca gagatggccc catccagtca ccacatccac ttctcatcca      360
gagatgtctg tttcttggca cgctggggta aattaggaca gaaggtgaca gtcttgggtg      420
tggtcagtca gactgcccca ggcaggcctt gtggcctgta gaaaacgttc aggcctaggc      480
cgggcacggt ggctcacgcc tgtaatccca gcactttggg aggccgaggc gggtggatca      540
cgaggtcagg agatcgtgac catcctggct aacacggtga accccgtctc tactaaaaa      600 tacaaaaaat tggccgggca tggtggcggg cacctgtagt tccagctact cgggaggctg      660
aggcaggaga atggcgtgaa cccgagaggc agagtttgca gtgagccgag atcgcgccac      720
tgcactccag cctgggcgac agagcaagac tccatctgga aaagaaaaag aaaacgttca      780
ggtctgagcc agaggcccag gctgtaattc tgtcacttac catgaccttg ggcaaggcac      840
ttccttccct ggcccagttc acggggttgg aatcgactcc aaggtccctt ccagcattaa      900
cgctgcatgg ttctaagatg agaagatggg gcagtttccc ctctctcacc ccagcccgtg      960
tccacttcaa ggtgaatgac cagggaagtc acgtgtccca atcccgcagt tccaaagccc     1020
ttggggaccc tactgtcagg gtcgtgcacg aggaggtgaa ggtcaggtga gccaatcgcc     1080
tcgaagggtc ttgcctcatt cggacagac atccggtttc ctctggctct accgggattc     1140
taggggcttt agccgaatga gtcatggggg gcggggggt ttctgggggga gttcccagct     1200 aatcaacttg ggacaggaca gcctggaact ttcgatggtg cctatccaag tg            1252
```

<210> SEQ ID NO 8
<211> LENGTH: 14
<212> TYPE: DNA
<213> ORGANISM: Homo sapiens
<220> FEATURE:
<221> NAME/KEY: misc_feature
<222> LOCATION: (1)...(14)

-continued

```
<223> OTHER INFORMATION: n = A,T,C or G

<400> SEQUENCE: 8
yyyyyyyyyy nyag                                                              14
```